US010231905B2

(12) United States Patent
Kawashima et al.

(10) Patent No.: US 10,231,905 B2
(45) Date of Patent: Mar. 19, 2019

(54) DENTAL CURABLE COMPOSITION

(71) Applicant: KURARAY NORITAKE DENTAL INC., Kurashiki-shi (JP)

(72) Inventors: Mitsunobu Kawashima, Tainai (JP); Mitsuru Takei, Yokohama (JP); Naoki Nishigaki, Tainai (JP); Shumei Ishihara, Tainai (JP); Kenji Hatanaka, Tainai (JP); Hiroshige Ishino, Tainai (JP); Akiko Tsuji, Kurashiki (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 14/778,851

(22) PCT Filed: Mar. 25, 2014

(86) PCT No.: PCT/JP2014/001726
§ 371 (c)(1),
(2) Date: Sep. 21, 2015

(87) PCT Pub. No.: WO2014/156138
PCT Pub. Date: Oct. 2, 2014

(65) Prior Publication Data
US 2016/0038382 A1    Feb. 11, 2016

(30) Foreign Application Priority Data
Mar. 26, 2013    (JP) ................. 2013-064810

(51) Int. Cl.
| A61K 6/083 | (2006.01) |
| A61K 6/097 | (2006.01) |
| A61K 6/08 | (2006.01) |

(52) U.S. Cl.
CPC ............ *A61K 6/083* (2013.01); *A61K 6/08* (2013.01); *A61K 6/0835* (2013.01); *A61K 6/097* (2013.01)

(58) Field of Classification Search
USPC .............................. 523/116, 118; 433/228.1
See application file for complete search history.

(56) References Cited

U.S. PATENT DOCUMENTS

| 3,471,613 | A | * | 10/1969 | Gagolski | A61K 8/55 424/57 |
| 5,049,375 | A | | 9/1991 | Tsujita et al. | |
| 5,130,146 | A | | 7/1992 | Tsujita et al. | |
| 5,744,511 | A | | 4/1998 | Kazama et al. | |
| 7,977,405 | B2 | * | 7/2011 | Ishino | A61K 6/0023 523/116 |
| 8,591,867 | B2 | | 11/2013 | Oshino et al. | |
| 8,999,298 | B2 | | 4/2015 | Yoshida et al. | |
| 9,186,433 | B2 | * | 11/2015 | Yoshida | A61K 6/0023 |
| 2003/0136303 | A1 | | 7/2003 | Kobayashi et al. | |
| 2005/0009946 | A1 | | 1/2005 | Oguri et al. | |
| 2008/0015279 | A1 | | 1/2008 | Tokui et al. | |
| 2012/0321596 | A1 | | 12/2012 | Yoshida et al. | |
| 2013/0172441 | A1 | | 7/2013 | Takahata et al. | |
| 2016/0030627 | A1 | | 2/2016 | Yoshida et al. | |

FOREIGN PATENT DOCUMENTS

| CA | 2254649 A1 | 6/1999 |
| CA | 2254355 A1 | 5/2000 |
| JP | 57-88106 A | 6/1982 |
| JP | 3-72415 A | 3/1991 |
| JP | 8-104696 A | 4/1996 |
| JP | 9-3109 A | 1/1997 |
| JP | 10-245525 A | 9/1998 |
| JP | 11-268929 A | 10/1999 |
| JP | 11-315214 A | 11/1999 |
| JP | 2003-96122 A | 4/2003 |
| JP | 2009-167135 A | 7/2009 |
| WO | WO 2004/060336 A1 | 7/2004 |
| WO | WO 2009/091001 A1 | 7/2009 |
| WO | WO 2011/102530 * | 8/2011 |
| WO | WO 2012/042911 A1 | 4/2012 |
| WO | WO 2013/099940 A1 | 7/2013 |
| WO | WO 2014/050144 A1 | 4/2014 |

OTHER PUBLICATIONS

Extended European Search Report dated Jul. 28, 2016 in Patent Application No. 14773187.1.
International Search Report dated Jul. 1, 2014, in PCT/JP2014/001726 filed Mar. 25, 2014.

* cited by examiner

*Primary Examiner* — Tae H Yoon
(74) *Attorney, Agent, or Firm* — Oblon, McClelland, Maier & Neustadt, L.L.P.

(57) ABSTRACT

The present invention relates to providing a dental curable composition that, when cured, has high metal ion release ability and highly durable physical properties. The dental curable composition of the present invention includes: a sugar compound having an —XM group, where —X is an acid anion group and M is a metal cation; and a curable component.

14 Claims, No Drawings

DENTAL CURABLE COMPOSITION

CROSS-REFERENCE TO RELATED APPLICATIONS

This application is a 371 National Stage Application, which claims the benefit of International Application No. PCT/JP2014/001726, filed on Mar. 25, 2014, which claims priority to Japanese Patent Application No. 2013-064810, filed on Mar. 26, 2013, the contents of which are hereby incorporated by references in their entirety.

TECHNICAL FIELD

The present invention relates to a dental curable composition that, when cured, has high metal ion release ability and has highly durable physical properties.

BACKGROUND ART

In dental treatment of caries, the carious part is first removed, and then the lost part is filled with a curable composition in order to restore the shape and function of the tooth. Widely used examples of the curable composition for filling are composite resins, glass ionomer cements, and resin-modified glass ionomer cements, which are used in combination with dental adhesives. When the lost part is large, a restorative prosthesis called an inlay, an onlay, or a crown, which is produced from a metal, a ceramic, a cured composite resin or the like, is attached to the lost part. In attaching the restorative prosthesis to the lost part, a curable composition called a luting cement is used. Widely used examples of the curable composition for luting are compositions such as resin cements, glass ionomer cements, and resin-modified glass ionomer cements.

A restored part of a tooth needs to have long-term durability. To this end, it is required that the restorative material used itself, which is a cured product of a curable composition, be capable of stably maintaining its physical properties in the oral cavity over a long period of time, and that formation of a gap between the restorative material and the tooth be reduced to prevent secondary caries from occurring in the gap between the restorative material and the tooth. To meet these requirements, technical improvements have been attempted in terms of strengthening of the restorative material itself or strengthening of adhesion between the restorative material and the tooth structure.

It has been widely known that fluorine is effective in preventing the occurrence of caries, and there are disclosed techniques aimed at preventing the occurrence of second caries by endowing a restorative material with fluorine release ability so as to strengthen the surface of a tooth that is in contact with the restorative material as well as by reducing the formation of a gap between the restorative material and the tooth with improved bonding technology.

Fluorine is a useful substance for strengthening a tooth structure; however, under recent circumstances where a restorative method with the least possible use of teeth scraping is increasingly demanded for conservation of teeth, metal ion release from a restorative material is also demanded in treatment of early caries or restoration to a condition with slight remaining caries in order to restore a tooth tissue by remineralization or increase the strength of the tooth tissue.

Conventionally-known approaches for endowing a dental curable composition with metal ion release ability include addition of a water-soluble metal salt and addition of a metal ion-releasing filler (see Patent Literature 1 and 2). In the case of the addition of a water-soluble metal salt, metal ion release can easily be achieved as a result of dissolution of the water-soluble metal compound in a liquid such as saliva; however, there is a problem in that the physical properties such as the mechanical strength and bond strength of the cured product of the dental curable composition (restorative material) are markedly deteriorated with the leaching of the metal ions, leading to fracture, detachment or the like of the restorative material. In the case where a metal ion-releasing filler with low solubility in water is added so as to avoid the deterioration in the physical properties of the restorative material, the amount of ions leached from the restorative material is small, and effective action on strengthening of a tooth structure cannot be obtained.

A combination of hydroxyapatite particles with a calcium sugar phosphate is known to be effective in treatment of relatively early caries such as C1 and C2 caries, root caries, hyperesthesia, etc. (see Patent Literature 3). The technique described in Patent Literature 3 consists of restoring a tooth by injection or application of a hydroxyapatite particle-containing composition to a damaged part of a tooth surface, followed by impregnation with a calcium sugar phosphate-containing composition to bond the hydroxyapatite particles together via the calcium sugar phosphate. That is, the technique described in Patent Literature 3 is one established merely by combined use with hydroxyapatite particles, and lacks the technical idea of adding a curable component to a composition.

There is also known a sugar phosphate capable of reacting with a mineral to form a complex (see Patent Literature 4). Additionally, Patent Literature 4 discloses an oral composition containing the sugar phosphate. The oral composition described in Patent Literature 4, however, is one that undergoes formation of a complex of the sugar phosphate with calcium and thereby prevents the occurrence of calculus due to deposition of calcium on teeth. That is, the technique relates to inhibition of calcification involving calcium.

CITATION LIST

Patent Literature

Patent Literature 1: JP 11(1999)-315214 A
Patent Literature 2: JP 11(1999)-268929 A
Patent Literature 3: JP 2009-167135 A
Patent Literature 4: JP 8(1996)-104696A

SUMMARY OF INVENTION

Technical Problem

The present invention aims to provide a dental curable composition that, when cured, has high metal ion release ability and has highly durable physical properties.

Solution to Problem

The present invention successfully solving the above problems is a dental curable composition including: a sugar compound having an —XM group, where —X is an acid anion group and M is a metal cation; and a curable component.

In the present invention, it is preferable that —X in the —XM group of the sugar compound be at least one acid anion group selected from the group consisting of: a carboxylate anion group represented by —COO$^{31}$; phosphorus atom-containing acid anion groups represented by —P(=O)(—O⁻)$_2$, —P(=O)(—OR)(—O⁻), —O—P(=O)(—O³¹)$_2$, and —O—P(=O)(—OR)(—O⁻), where R represents an alkyl group or an optionally substituted aromatic group; sulfur atom-containing acid anion groups represented by —SO$_2^{31}$, —SO$_3^{31}$, and —O—SO$_3^{31}$; and boron atom-containing acid anion groups represented by —B(O⁻)$_2$, —O—B(O⁻)$_2$, —B(—OR)(O⁻), and —O—B(—OR)(O⁻), where R represents an alkyl group or an optionally substituted aromatic group, and M in the —XM group of the sugar compound be a calcium ion, a strontium ion, or an aluminum ion.

In the present invention, it is preferable that the sugar compound having the —XM group be a calcium sugar phosphate. The dental curable composition of the present invention preferably contains 0.01 to 30 weight % of the sugar compound having the —XM group.

In a preferred embodiment of the present invention, the curable component includes a polymerizable monomer (a) having no acidic group and a polymerization initiator (b). In this embodiment, the curable component may further include an acidic group-containing polymerizable monomer (d). In addition, the dental curable composition of the present invention may further include a filler (c).

In a preferred embodiment of the present invention, the curable component includes a polyalkenoic acid (e), an ion-leachable glass (f), and water (g). In this embodiment, the curable component may further include a polymerizable monomer (a) having no acidic group and a polymerization initiator (b). In addition, the curable component may further include an acidic group-containing polymerizable monomer (d).

The dental curable composition of the present invention can be suitably used in a dental restorative filling material, a dental adhesive material, a dental luting material, a dental temporary sealing material, a dental pit and fissure sealant, etc.

Advantageous Effects of Invention

A cured product of the dental curable composition of the present invention has high metal ion release ability and highly durable physical properties. Particularly, despite releasing metal ions, the cured product has highly durable adhesive properties to a tooth structure and a dental prosthesis, and can maintain a high level of mechanical strength over a long period of time. The dental curable composition of the present invention can be composed to release metal ions useful, for example, for prevention of caries by tooth structure strengthening and for repair of early caries. The dental curable composition of the present invention can be suitably used in a dental restorative filling material, a dental adhesive material, a dental luting material, a dental temporary sealing material, a dental pit and fissure sealant, etc.

DESCRIPTION OF EMBODIMENTS

The dental curable composition of the present invention includes: a sugar compound having an —XM group, where —X is an acid anion group and M is a metal cation; and a curable component.

First, the sugar compound having the 13 XM group which is used in the present invention will be described. In the —XM group of the sugar compound, —X represents an acid anion group. The term "acid anion group" as used herein refers to an anionic group formed by desorption of one or more protons (H⁺) from an acid group. Specific examples of the acid anion group represented by —X include: a carboxylate anion group represented by —COO⁻; phosphorus atom-containing acid anion groups represented by —P(=O)(—O⁻)$_2$, —P(=O)(—OR)(—O⁻), —O—P(=O)(—O⁻)$_2$, and —O—P(=O)(—OR)(—O⁻), where R represents an alkyl group or an optionally substituted aromatic group; sulfur atom-containing acid anion groups represented by —SO$_2^-$, —SO$_3^-$, and —O—SO$_3^-$; and boron atom-containing acid anion groups represented by —B(O⁻)$_2$, —O—B(O⁻)$_2$, —B(—OR)(O⁻), and —O—B(—OR)(O³¹), where R represents an alkyl group or an optionally substituted aromatic group.

The alkyl group represented by R may be linear, branched, or cyclic, and preferably has 1 to 6 carbon atoms. Specific examples of the alkyl group include methyl, ethyl, n-propyl, isopropyl, n-butyl, isobutyl, t-butyl, n-pentyl, isopentyl, hexyl, and cyclohexyl. Preferred are methyl and ethyl. Examples of the optionally substituted aromatic group represented by R include: a phenyl group optionally substituted with an alkyl group having 1 to 3 carbon atoms, a halogen atom, or the like; and a naphthyl group optionally substituted with an alkyl group having 1 to 3 carbon atoms, a halogen atom, or the like. Specific examples of the aromatic group include phenyl, 4-methylphenyl, 3,5-dimethylphenyl, 3-chlorophenyl, 4,5-dichlorophenyl, 1-naphthyl, and 2-naphthyl. Preferred is phenyl.

The sugar compound having the —XM group which is used in the present invention may contain only one type of —X or two or more types of —X. The acid anion group represented by —X is preferably a phosphorus atom-containing acid anion group, more preferably a phosphate anion group, and even more preferably a group represented by —O—P(=O)(—O⁻)$_2$, in terms of the balance between binding properties to the metal cation and water solubility The type of the metal cation represented by M in the XM group is not particularly limited as long as it is a cation of a metal element applicable for dental use. Preferably, the metal cation is a cation of a metal element that is a major component of a tooth tissue itself, a cation of a metal element that is known to have the effect of promoting mineralization of a tooth tissue, or a cation of a metal element that is known to endow a tooth tissue with acid resistance by being incorporated in the tooth tissue. Specific examples of the cation of the metal element that is a major component of a tooth tissue itself include a calcium ion. Specific examples of the cation of the metal element that is known to have the effect of promoting mineralization of a tooth tissue include a strontium ion. Specific examples of the cation of the metal element that is known to endow a tooth tissue with acid resistance include an aluminum ion.

The sugar compound having the —XM group which is used in the present invention may contain only one type of M or may contain two or more types of M. M is preferably a calcium ion, a strontium ion, or an aluminum ion. The calcium ion, which is a cation of a major constituent element of a natural tooth, is most preferable in terms of strengthening of a tooth structure. M may be bonded to one —X group or may be bonded to two or more —X groups.

The type of the sugar skeleton of the sugar compound used in the present invention is not particularly limited as long as the sugar skeleton is a sugar structure into which the —XM group can be introduced. For efficient achievement of the effect of the present invention, the sugar constituting the skeleton is preferably an oligosaccharide or a polysaccharide. Examples thereof include lactose, sucrose, sucralose, cellobiose, trehalose, maltose, palatinose, maltotriose, maltodextrin, cyclodextrin, glycosylsucrose, amylose, amylopectin, cycloamylose, glycogen, glucan, cellulose, agarose, cluster dextrin, mannan, and pullulan. One of these may be used alone or two or more thereof may be used in combination.

In a preferred embodiment, the sugar compound having the —XM group which is used in the present invention includes glucan as the sugar constituting the skeleton and has at least one —XM group per glucan molecule, and —X is a phosphate anion group.

In another preferred embodiment, the sugar compound having the —XM group which is used in the present invention includes glucan as the sugar constituting the skeleton, the glucan is composed of 3 to 5 glucose molecules linked by α-1,4 bonds, one —XM group is bonded to the glucan, and —X is a phosphate anion group.

In still another preferred embodiment, the sugar compound having the —XM group which is used in the present invention includes glucan as the sugar constituting the skeleton, the glucan is composed of 2 to 8 glucose molecules linked by α-1,4 bonds, two —XM groups are bonded to the glucan, and —X is a phosphate anion group.

In still another preferred embodiment, the sugar compound having the —XM group which is used in the present invention includes glucan as the sugar constituting the skeleton, and the glucan has a main chain composed of glucose molecules linked by α-1,4 bonds and a side chain composed of glucose molecules linked by α-1,6 bonds and/or α-1,4 bonds.

Preferably, the sugar skeleton of the sugar compound having the —XM group which is used in the present invention is glucan composed of 2 to 8 glucose molecules linked by α-1,4 bonds.

In the sugar compound having the —XM group which is used in the present invention, the preferred number of the —XM groups is 1 to 2.

In the sugar compound having the —XM group which is used in the present invention, the preferred number of the cations M is equal to the number of the —X groups.

In an embodiment of the present invention, the sugar compound having the —XM group is more preferably a calcium sugar phosphate. That is, —X is a phosphate anion group and M is a calcium ion. More preferably, the calcium sugar phosphate includes as a sugar skeleton glucan composed of 2 to 8 glucose molecules linked by α-1,4 bonds, the glucan has 1 to 2 phosphate anion groups, and the number of the calcium ions is 1 to 2. Even more preferably, the number of the phosphate anion groups and the number of the calcium ions in the calcium sugar phosphate are equal.

In the present invention, one type of the sugar compound having the —XM group may be used alone, or a mixture of two or more types of the sugar compounds having the —XM group may be used.

When the calcium sugar phosphate, which is a suitable example of the sugar compound having the —XM group, is produced according to the method described in Patent Literature 4, the calcium sugar phosphate is obtained in the form of a mixture of two or more types of calcium sugar phosphates. In the present invention, the mixture may as such be used. Alternatively, the mixture may be separated into different compounds, and then only one of the compounds may be selected and used.

In the dental curable composition of the present invention, the preferred content of the sugar compound having the —XM group is 0.01 to 30 weight % relative to the total amount of the composition. If the content of the sugar compound having the —XM group is too low, the amount of metal ion release will be small, which may lead to a situation where a sufficient level of expected effect on strengthening a tooth structure cannot be obtained. Conversely, too high a content of the sugar compound, although providing a large amount of metal ion release, may reduce the mechanical strength of the cured product of the dental curable composition, thereby impairing the function required for use as a restorative material. The content of the sugar compound having the —XM group is more preferably 0.05 to 20 weight %, even more preferably 0.1 to 10 weight %, particularly preferably 0.2 to 8 weight %, and most preferably 1 to 6 weight %.

The dental curable composition of the present invention includes a curable component in addition to the sugar compound having the —XM group. The type of the curable component varies depending on the use of the composition. Therefore, the curable component will now be described for different uses. Additionally, the dental curable composition of the present invention may include optional components for the purpose of property improvement or the like, and such optional components will also be described.

Examples of the use of the dental curable composition of the present invention include uses as: a dental composite resin, a dental adhesive, a dental resin cement, a dental glass ionomer cement, a dental resin-modified glass ionomer cement, and a dental quick cure resin which are used in a dental restorative filling material, a dental adhesive material, a dental luting material, a dental temporary sealing material, a dental provisional crown material, and a dental pit and fissure sealant.

The dental composite resin, the dental adhesive, the dental resin cement, and the dental quick cure resin are each classified as a resin-based material. The resin-based material includes, as an essential component, a curable component including a polymerizable monomer (a) having no acidic group and a polymerization initiator (b). The resin-based material undergoes curing reaction induced by the fact that an active species such as a radical produced from the polymerization initiator binds to a double bond of the polymerizable monomer through an addition reaction.

The polymerizable monomer (a) having no acidic group in the present invention is specifically a polymerizable monomer having a polymerizable unsaturated group such as a (meth)acryloyl group, a vinyl group, or a styrene group and having no acidic group. The polymerizable monomer forms a polymer as a result of radial polymerization reaction triggered by the polymerization initiator (b) described later. The polymerizable monomer (a) having no acidic group is preferably a (meth)acrylic acid ester or a (meth)acrylamide derivative, and is more preferably a (meth)acrylic acid ester. The expression "(meth)acryl" in the present invention is used to include both methacryl and acryl. Polymerizable monomers can be broadly classified into monofunctional polymerizable monomers and crosslinking polymerizable monomers. Examples of the polymerizable monomers which are (meth)acrylic acid esters or (meth)acrylamide derivatives are given below. Examples of the monofunctional polymerizable monomers include methyl (meth)acrylate, isobutyl (meth)acrylate, benzyl (meth)acrylate, lauryl (meth)acrylate, 2-(N,N-dimethylamino)ethyl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono(meth)acrylate, glycerin mono(meth)acrylate, erythritol mono (meth)acrylate, N-methylol (meth)acrylamide, N-hydroxyethyl (meth)acrylamide, N-(dihydroxyethyl) (meth)acrylamide, (meth)acryloyloxydodecylpyridinium bromide, (meth)acryloyloxydodecylpyridinium chloride, (meth)acryloyloxyhexadecylpyridinium chloride, (meth) acryloyloxydecylammonium chloride, and 10-mercaptodecyl (meth)acrylate.

Examples of the crosslinking polymerizable monomers include an aromatic-based difunctional polymerizable monomer, an aliphatic-based difunctional polymerizable monomer, and a tri- or higher-functional polymerizable monomer.

Examples of the aromatic-based difunctional polymerizable monomer include: 2,2-bis((meth)acryloyloxyphenyl) propane, 2,2-bis[4-(3-(meth)acryloyloxy-2-hydroxypropoxy)phenyl]propane (generally called "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl) pyromellitate. Among these, 2,2-bis[4-(3-methacryloyloxy-2-hydroxypropoxy)phenyl] propane and 2,2-bis(4-methacryloyloxypolyethoxyphenyl) propane are preferable.

Examples of the aliphatic-based difunctional polymerizable monomer include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate (particularly polyethylene glycol di(meth)acrylate having nine or more oxyethylene groups), 1,3-butanediol di(meth)acrylate, 1,5-pentanediol di(meth)acrylate, 1,6-hexane diol di(meth)acrylate, 1,10-decanediol di(meth)acrylate, 2,2,4-trimethylhexamethylene bis(2-carbamoyloxyethyl) dimethacrylate (generally called "UDMA"), and 1,2-bis(3-methacryloyloxy-2-hydroxypropyloxy)ethane. Among these, glycerol dimethacrylate, triethylene glycol dimethacrylate, neopentyl glycol dimethacrylate, 2,2,4-trimethylhexamethylene bis(2-carbamoyloxyethyl) dimethacrylate, and 1,2-bis(3-methacryloyloxy-2-hydroxypropyloxy)ethane are preferable.

Examples of the tri- or higher-functional polymerizable monomer include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate, N,N-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane.

Any one of the above polymerizable monomers (a) having no acidic group may be contained alone, or a combination of two or more types of the polymerizable monomers (a) may be contained.

A polymerization initiator selected from those used in general industry can be used as the polymerization initiator (b). Particularly, a polymerization initiator for dental use is preferably used. A polymerization initiator for chemical polymerization and/or photopolymerization is used alone or two or more such polymerization initiators are used in appropriate combination. A combination of an oxidant and a reductant is preferably used as a chemical polymerization initiator. Examples of the oxidant include organic peroxides, azo compounds, and inorganic peroxides.

Examples of the organic peroxides include diacyl peroxides, peroxyesters, peroxycarbonates, dialkyl peroxides, peroxyketals, ketone peroxides, and hydroperoxides. Specific examples of the diacyl peroxides include benzoyl peroxide, 2,4-dichlorobenzoyl peroxide, m-toluoyl peroxide, and lauroyl peroxide. Specific examples of the peroxyesters include t-butyl peroxybenzoate, bis-t-butyl peroxyisophthalate, and t-butyl peroxy-2-ethylhexanoate. Specific examples of the peroxycarbonates include t-butyl peroxy isopropyl carbonate. Specific examples of the dialkyl peroxides include dicumyl peroxide, di-t-butyl peroxide, and 2,5-dimethyl-2,5-bis(benzoylperoxy)hexane. Specific examples of the peroxyketals include 1,1-bis(t-butylperoxy)-3,3,5-trimethylcyclohexane, 1,1-bis(t-butylperoxy)cyclohexane, and 1,1-bis(t-hexylperoxy)cyclohexane. Specific examples of the ketone peroxides include methyl ethyl ketone peroxide, cyclohexanone peroxide, and methyl acetoacetate peroxide. Specific examples of the hydroperoxides include t-butyl hydroperoxide, cumene hydroperoxide, diisopropylbenzene hydroperoxide, and 1,1,3,3-tetramethylbutyl hydroperoxide.

Examples of the azo compounds include azobisisobutyronitrile and azobisisobutylvaleronitrile.

Examples of the inorganic peroxides include sodium persulfate, potassium persulfate, aluminum persulfate, and ammonium persulfate.

Examples of the reductant include aromatic amines having no electron-withdrawing group in the aromatic ring, thioureas, and ascorbic acid.

Examples of the aromatic amines having no electron-withdrawing group in the aromatic ring include aromatic amine compounds in which any hydrogen atom of the aromatic ring has not been substituted by an electron-withdrawing group such as a carboxylic acid group, a carboxylic acid ester group, a nitrile group, or a halogen group. Specific examples of such compounds include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethy)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. Any one of the above aromatic amines having no electron-withdrawing group in the aromatic ring may be used alone or two or more thereof may be used in combination.

Examples of the thioureas include thiourea, methylthiourea, ethylthiourea, N,N'-dimethylthiourea, N,N'-diethylthiourea, N,N'-di-n-propylthiourea, dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea. Any one of the above thioureas may be contained alone or two or more thereof may be used in combination.

The chemical polymerization initiator may be a combination of the oxidant, the reductant, and an optionally added polymerization accelerator. Examples of the polymerization accelerator include aliphatic amines, aromatic tertiary amines containing an electron-withdrawing group, sulfinic acids and/or salts thereof, reducible inorganic compounds containing sulfur, reducible inorganic compounds containing nitrogen, borate compounds, barbituric acid derivatives, triazine compounds, copper compounds, tin compounds, vanadium compounds, halogen compounds, aldehydes, and thiol compounds.

Examples of the aliphatic amines which may be used as the polymerization accelerator in the chemical polymerization initiator include primary aliphatic amines such as n-butylamine, n-hexylamine, and n-octylamine; secondary aliphatic amines such as diisopropylamine and dibutylamine; and tertiary aliphatic amines such as N-methyldiethanolamine, N-ethyldiethanolamine, N-n-butyldiethanolamine, N-lauryldiethanolamine, 2-(dimethylamino)ethyl (meth)acrylate, N-methyldiethanolamine di(meth)acrylate, N-ethyldiethanolamine di(meth)acrylate, triethanolamine mono(meth)acrylate, triethanolamine di(meth)acrylate, triethanolamine tri(meth)acrylate, triethanolamine, trimethylamine, triethylamine, and tributylamine. Among these, the tertiary aliphatic amines are preferable in terms of the curability and storage stability of the composition. Among the tertiary aliphatic amines, N-methyldiethanolamine and triethanolamine are preferable.

Examples of the electron withdrawing group-containing aromatic tertiary amines which may be used as the polymerization accelerator in the chemical polymerization initiator include aromatic tertiary amine compounds in which a hydrogen atom of the aromatic ring has been substituted by an electron-withdrawing group such as a carboxylic acid group, a carboxylic acid ester group, a nitrile group, a halogen group, or an acyl group. Specific examples of the compounds include ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino)benzoate, and 4-(N,N-dimethylamino) benzophenone. Among these, ethyl 4-(N,N-dimethylamino)benzoate, methyl 4-(N,N-dimethylamino)benzoate, n-butoxyethyl 4-(N,N-dimethylamino)benzoate, and 4-(N,N-dimethylamino)benzophenone are preferable in terms of the curability of the composition.

Specific examples of the sulfinic acids and/or salts thereof which may be used as the polymerization accelerator in the chemical polymerization initiator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate.

Examples of the sulfur-containing reducible inorganic compounds which may be used as the polymerization accelerator in the chemical polymerization initiator include sulfurous acid salts, bisulfurous acid salts, pyrosulfurous acid salts, thiosulfuric acid salts, thionic acid salts, and dithionous acid salts. Specific examples include sodium sulfite, potassium sulfite, calcium sulfite, ammonium sulfite, sodium hydrogen sulfite, and potassium hydrogen sulfite.

Examples of the nitrogen-containing reducible inorganic compounds which may be used as the polymerization accelerator in the chemical polymerization initiator include nitrous acid salts, and specific examples include sodium nitrite, potassium nitrite, calcium nitrite, and ammonium nitrite.

The borate compound used as the polymerization accelerator in the chemical polymerization initiator is preferably an aryl borate compound. Specific examples of aryl borate compounds, particularly aryl borate compounds having one aryl group per molecule, which can be suitably used include: trialkylphenylboron, trialkyl(p-chlorophenyl)boron, trialkyl(p-fluorophenyl)boron, trialkyl(3,5-bistrifluoromethyl)phenylboron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (their alkyl groups are at least one selected from the group consisting of an n-butyl group, an n-octyl group, an n-dodecyl group, and the like); and salts thereof (sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts, etc.).

Examples of the borate compounds that have two aryl groups per molecule include: dialkyldiphenylboron, dialkyldi(p-chlorophenyl)boron, dialkyldi(p-fluorophenyl)boron, dialkyldi(3,5-bis-trifluoromethyl)phenylboron, dialkyldi[3,5-bis(1,1,1,3,3,3-hexafluoro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron, and dialkyldi(m-octyloxyphenyl)boron (their alkyl groups are at least one selected from the group consisting of an n-butyl group, an n-octyl group, an n-dodecyl group, and the like); and salts thereof (sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts, etc.).

Furthermore, examples of the borate compounds that have three aryl groups per molecule include: monoalkyltriphenylboron, monoalkyltri(p-chlorophenyl)boron, monoalkyltri(p-fluorophenyl)boron, monoalkyltri(3,5-bis-trifluoromethyl)phenylboron, monoalkyltri[3,5-bis(1,1,1,3,3,3-hexafluoro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl)boron (their alkyl groups are at least one selected from an n-butyl group, an n-octyl group, an n-dodecyl group, and the like); and salts thereof (sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts, etc.).

Furthermore, examples of the borate compounds that have four aryl groups per molecule include: tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl] boron, tetrakis(p-nitrophenyl)boron, tetrakis(m-nitrophenyl) boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, (3,5-bistrifluoromethyl)phenyl triphenylboron, (p-nitrophenyl)triphenylboron, (m-butyloxyphenyl)triphenylboron, (p-butyloxyphenyl)triphenylboron, (m-octyloxyphenyl)triphenylboron, and (p-octyloxyphenyl)triphenylboron; and salts thereof (sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts, etc.).

Examples of the barbituric acid derivatives which may be used as the polymerization accelerator in the chemical polymerization initiator include: barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, and thiobarbituric acids; and salts thereof (preferably salts of alkali metals or alkaline earth metals). Examples of the salts of the barbituric acids include sodium 5-butylbarbiturate, sodium 1,3,5-trimethylbarbiturate, and sodium 1-cyclohexyl-5-ethylbarbiturate.

Examples of the triazine compounds which may be used as the polymerization accelerator in the chemical polymerization initiator include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-(α,α,β-trichloroethyl)-4,6-bis(trichloromethyl)-s-triazine, 2-styryl-4,6-bis(trichloromethyl)-s-triazine, 2-[2-(p-methoxyphenynethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Examples of the copper compounds which can be suitably used as the polymerization accelerator in the chemical polymerization initiator include copper acetylacetonate, copper (II) acetate, copper oleate, copper (II) chloride, and copper (II) bromide.

Examples of the tin compounds which may be used as the polymerization accelerator in the chemical polymerization initiator include di-n-butyltin dimaleate, di-n-octyltin dimaleate, di-n-octyltin dilaurate, and di-n-butyltin dilaurate. Among these, suitable tin compounds are di-n-octyltin dilaurate and di-n-butyltin dilaurate.

The vanadium compounds which may be used as the polymerization accelerator in the chemical polymerization initiator are preferably compounds of tetravalent and/or pentavalent vanadium. Examples of the compounds of tetravalent and/or pentavalent vanadium include compounds disclosed in JP 2003-96122 A, such as divanadium (IV) tetroxide, vanadium (IV) oxide acetylacetonate, vanadyl (IV) oxalate, vanadyl (IV) sulfate, oxobis(1-phenyl-1,3-butanedionato)vanadium (IV), bis(maltolato)oxovanadium (IV), vanadium (V) pentoxide, sodium metavanadate (V), and ammonium metavanadate (V).

Examples of the halogen compounds which can be suitably used as the polymerization accelerator in the chemical polymerization initiator include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes which may be used as the polymerization accelerator in the chemical polymerization initiator include terephthalaldehyde and benzaldehyde derivatives. Examples of the benzaldehyde derivatives include dimethylbenzaldehyde, p-methyloxybenzaldehyde, p-ethyloxybenzaldehyde, and p-n-octyloxybenzaldehyde.

Examples of the thiol compounds which may be used as the polymerization accelerator in the chemical polymerization initiator include 3-mercaptopropyltrimethoxysilane, 2-mercaptobenzoxazole, decanethiol, and thiobenzoic acid.

These polymerization accelerators may be used alone or two or more thereof may be used in the chemical polymerization initiator. In terms of good storage stability, the polymerization accelerator is preferably at least one selected from the group consisting of ethyl 4-(N,N-dimethylamino) benzoate, methyl 4-(N,N-dimethylamino)benzoate, n-butoxyethyl 4-(N,N-dimethylamino)benzoate, 4-N,N-dimethylaminobenzophenone, sodium benzenesulfinate, sodium p-toluenesulfinate, sodium 2,4,6-trimethylbenzenesulfinate, sodium 2,4,6-triisopropylbenzenesulfinate, sodium sulfite, potassium sulfite, calcium sulfite, ammonium sulfite, sodium hydrogen sulfite, and potassium hydrogen sulfite.

Examples of the initiator for photopolymerization include (bis)acylphosphine oxides, α-diketones, and coumarins.

Examples of the (bis)acylphosphine oxides, particularly acylphosphine oxides, which may be used as the photopolymerization initiator include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2,6-dimethylphenyl)phosphonate, (2,5,6-trimethylbenzoyl)-2,4,4-trimethylpentylphosphine oxide, and 2,4,6-trimethylbenzoylphenylphosphine oxide sodium salt. Examples of the bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoy)phenylphosphine oxide, bis(2,6-dimethoxybenzoy)-2,4,4-trimethylpentylphosphine oxide, bis(2,6-dimethoxybenzoyl)-2,5-dimethylphenylphosphine oxide, and bis(2,4,6-trimethylbenzoy)phenylphosphine oxide.

Among these (bis)acylphosphine oxides, 2,4,6-trimethylbenzoyldiphenylphosphine oxide, 2,4,6-trimethylbenzoylmethoxyphenylphosphine oxide, bis(2,4,6-trimethylbenzoynphenylphosphine oxide, and 2,4,6-trimethylbenzoylphenylphosphine oxide sodium salt are preferable.

Examples of the α-diketones which may be used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is suitable.

Examples of the coumarins which may be used as the photopolymerization initiator include compounds disclosed in JP 9(1997)-3109 A and JP 10(1998)-245525 A, such as 3,3'-carbonylbis(7-diethylamino)coumarin, 3-(4-methoxybenzoyl)coumarin, 3-thenoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl)coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphto[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrano[6,7,8-ij]quinolizin-11-one, and 10-(2-benzothiazoyl)-2,3,6,7-tetrahydro-1,1,7,7-tetramethyl-1H, 5H, 11H-[1]benzopyrano[6,7,8-ij]quinolizin-11-one.

Among the above coumarin compounds, 3,3'-carbonylbis(7-diethylaminocoumarin) and 3,3'-carbonylbis(7-dibutylaminocoumarin) are suitable.

Among these photopolymerization initiators, at least one selected from the group consisting of (bis)acylphosphine oxides, α-diketones, and coumarins that are widely used in dental curable compositions is preferably used.

Where necessary, such a photopolymerization initiator may further contain a polymerization accelerator; in this case, the photopolymerization may be efficiently performed in a short time.

Major examples of polymerization accelerators which can be suitably used in the photopolymerization initiator include tertiary amines, aldehydes, thiol group-containing compounds, and sulfinic acids and/or salts thereof.

Examples of the tertiary amines which may be used as the polymerization accelerator in the photopolymerization initiator include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethy)-4-t-butylaniline, N,N-bis(2-hydroxyethyl)-3,5-diisopropylaniline, N,N-bis(2-hydroxyethyl)-3,5-dibutylaniline, n-butoxyethyl 4-dimethylaminobenzoate, (2-methacryloyloxy)ethyl 4-dimethylaminobenzoate, ethyl 4-dimethylaminobenzoate, butyl 4-dimethylaminobenzoate, 4-dimethylaminobenzophenone, trimethylamine, triethylamine, N-methyldiethanolamine, N-ethyldiethanolamine, N-n-butyldiethanolamine, N-lauryldiethanolamine, triethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

Examples of the aldehydes which may be used as the polymerization accelerator in the photopolymerization initiator include dimethylbenzaldehyde and terephthalaldehyde.

Examples of the thiol group-containing compounds which may be used as the polymerization accelerator in the photopolymerization initiator include 2-mercaptobenzoxazole, decanethiol, 3-mercaptopropyltrimethoxysilane, and thiobenzoic acid.

Examples of the sulfinic acids and/or salts thereof which may be used as the polymerization accelerator in the photopolymerization initiator include benzenesulfinic acid, sodium benzenesulfinate, potassium benzenesulfinate, calcium benzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, and calcium 2,4,6-triisopropylbenzenesulfinate.

One type of the polymerization initiator (b) may be used alone or two or more types of the polymerization initiators (b) may be used in combination.

When the dental curable composition is used as a composite resin, the composition further contains a filler (c) in addition to the polymerizable monomer (a) having no acidic group and the polymerization initiator (b). Any of commonly-known inorganic particles used as a filler in dental composite resins can be used without any limitation. Specifically, for example, particles of the following conventionally-known materials can be used: various glass materials (containing silicon dioxide (quartz, quartz glass, silica gel, or the like) and silicon as main components and further containing heavy metal(s) and boron and/or aluminum); fluorine-containing glass materials such as fluoroaluminosilicate glass, calcium fluoroaluminosilicate glass, strontium fluoroaluminosilicate glass, barium fluoroaluminosilicate glass, and strontium calcium fluoroaluminosilicate glass; alumina; various ceramic materials; diatomite; kaolin; clay minerals (such as montmorillonite); activated white clay; synthetic zeolite; mica; silica; calcium fluoride; ytterbium fluoride; calcium phosphate; barium sulfate; zirconium dioxide (zirconia); titanium dioxide (titania); and hydroxyapatite. It is also acceptable to use organic-inorganic composite particles (organic-inorganic composite filler) obtained by adding the polymerizable monomer to any type of the above inorganic particles to form a paste, followed by polymerization and curing of the paste and then by pulverization of the cured product. One type of these inorganic particles may be used, or two or more types thereof may be used in combination.

Important physical properties required of a material for tooth crown restoration for which the composite resin may be used include radiographic visualizability comparable to that of natural teeth. To impart radiographic visualizability, an inorganic oxide containing a heavy metal element such as zirconium, barium, titanium, lanthanum, or strontium is used.

The form of the inorganic particles used as the filler (c) in the present invention is not particularly limited. For example, particles with any of various shapes such as a crushed shape, a sheet shape, a flake shape, a fiber shape (short-fiber shape or long-fiber shape), a needle shape, a whisker shape, and a spherical shape, are used. Also, the inorganic particles may be in the form of agglomerates composed of primary particles having any of the above shapes or may consist of a combination of particles having different shapes. In the present invention, the particles may be those that have been subjected to a process (e.g., pulverization) so as to have any of the above shapes.

The inorganic particles may have particle diameters appropriate for ordinary use as a filler in a dental composite resin. For example, the average particle diameter is 0.001 to 10 μm, and the particle diameter range extends from 0.0005 to 50 μm. In the present description, the average particle diameter of the inorganic particles refers to the average particle diameter of the primary particles of the inorganic particles (average primary particle diameter), and the particle diameter range refers to a range of particle diameters within which the particle diameters of 95% or more of the total particles used fall. The inorganic particles, even when accidentally including those falling outside the specified particle diameter range, can be used as long as the effect of the present invention is not impaired.

In the present description, the average particle diameter of the inorganic particles can be determined by laser diffraction scattering method or by electron microscope observation of the particles. Specifically, the laser diffraction scattering method is convenient for particle diameter measurement on particles with a diameter of not less than 0.1 μm, and the electron microscope observation is convenient for particle diameter measurement on ultrafine particles with a diameter of not more than 0.1 μm.

To be more specific about the laser diffraction scattering method, for example, the average particle diameter can be measured using a laser diffraction particle size distribution analyzer (SALD-2100, manufactured by Shimadzu Corporation) and using a 0.2% aqueous solution of sodium hexametaphosphate as a dispersion medium.

To be more specific about the electron microscope observation, for example, the average particle diameter can be determined by taking a photograph of particles with a transmission electron microscope (manufactured by Hitachi, Ltd., H-800NA) and measuring the particle diameters of particles (the number of which is 200 or more) observed within a unit area of visual field in the photograph by means of a particle size distribution analysis software of the image analysis type (Macview (Mountech Co., Ltd.)). In this case, the particle diameter of each particle is determined as an arithmetic mean of the maximum and minimum lengths of the particle, and, from the thus determined particle diameters and the number of the particles, the average primary particle diameter is calculated.

In the present invention, two or more types of inorganic particles differing in material, particle size distribution, and form, may be mixed or used in combination. Additionally, particles other than the inorganic particles may be accidentally contained as impurities to the extent that the other particles do not impair the effect of the present invention.

As the filler (c), there can also be used inorganic ultrafine particles having an average particle diameter of 0.001 to 0.1 μm and a specific surface area of 30 to 500 $m^2/g$ and serving as a modifier of the properties of the curable composition of the present invention that has yet to be cured or as a modifier of the strength and surface texture of the composition that has been cured. The average particle diameter of the inorganic ultrafine particles is preferably 0.005 to 0.05 μm, and more preferably 0.01 to 0.04 μm. The specific surface area of the inorganic ultrafine particles is preferably 40 to 400 $m^2/g$, and more preferably 50 to 200 $m^2/g$.

Such inorganic ultrafine particles are categorized as so-called nanoparticles (ultrafine particulate filler). Commonly-known inorganic ultrafine particles used in dental composite resins etc. can be used as the nanoparticles without any limitation. Preferred examples include: ultrafine particles of inorganic oxides such as silica, alumina, titania, and zirconia; ultrafine particles of composite oxides of said oxides; and ultrafine particles of calcium phosphate, hydroxyapatite, yttrium fluoride, ytterbium fluoride, barium titanate, and potassium titanate. More preferred are ultrafine particles of silica, alumina, titania, silica/alumina composite oxide, and silica/zirconia composite oxide which are prepared by flame pyrolysis. The shape of the inorganic ultrafine particles is not particularly limited, and can be selected as appropriate. When a commercialized product is available, it may be used as the filler (c) in the present invention. The commercialized product is not particularly limited, and examples of commercially-available ultrafine silica particles prepared by flame pyrolysis include Aerosil (trade name, manufactured by Nippon Aerosil Co., Ltd.).

The filler (c) used in the dental curable composition of the present invention is generally surface-treated beforehand in order to increase the mechanical strength of the resulting cured product. The surface treatment improves the compatibility between the surfaces of the inorganic particles and the polymerizable monomer, and also has the merit of improving the handling properties of the pasty composition that has yet to be cured.

A commonly-known surface treatment agent can be used as an agent for the surface treatment. There can be used: organometallic compounds such as organosilicon compounds, organotitanium compounds, organozirconium compounds, and organoaluminum compounds; and acidic group-containing organic compounds having at least one acidic group such as a phosphate group, a pyrophosphate group, a thiophosphate group, a phosphonate group, a sulfonate group, or a carboxylate group. When two or more surface treatment agents are used, the resulting surface-treated layer may be composed of a mixture of the two or more surface treatment agents or may have a multilayer structure composed of two or more stacked layers respectively consisting of the surface treatment agents. A commonly-known method for surface treatment can be used without particular limitation.

Examples of the organosilicon compounds include compounds represented by $R^1{}_n SiX_{4-n}$, where $R^1$ is a substituted or unsubstituted hydrocarbon group having 1 to 12 carbon atoms, X is an alkoxy group having 1 to 4 carbon atoms, a hydroxyl group, a halogen atom, or a hydrogen atom, and n is an integer of 0 to 3. When there are two or more $R^1$ and two or more X, the two or more $R^1$ may be the same as or different from each other, and the two or more X may be the same as or different from each other.

Specific examples include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(β-methoxyethoxy)silane, 3,3,3-trifluoropropyltrimethoxysilane, methyl-3,3,3-trifluoropropyldimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropylmethyldiethoxysilane, N-β(aminoethyl) γ-aminopropylmethyldimethoxysilane, N-β(aminoethyl) γ-aminopropyltrimethoxysilane, N-β(aminoethyl) γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyltrimethoxysilane (the number of carbon atoms between the (meth)acryloxy group and the silicon atom: 3 to 12, e.g., γ-methacryloxypropyltrimethoxysilane etc.), and ω-(meth)acryloxyalkyltriethoxysilane (the number of carbon atoms between the (meth)acryloxy group and the silicon atom: 3 to 12, e.g., γ-methacryloxypropyltriethoxysilane etc.). In the present invention, the expression "(meth)acryloxy" is used to include both methacryloxy and acryloxy.

Among those mentioned above, a coupling agent having a functional group copolymerizable with the polymerizable monomer is preferably used, and examples thereof include ω-(meth)acryloxyalkyltrimethoxysilane (the number of carbon atoms between the (meth)acryloxy group and the silicon atom: 3 to 12), ω-(meth)acryloxyalkyltriethoxysilane (the number of carbon atoms between the (meth)acryloxy group and the silicon atom: 3 to 12), vinyltrimethoxysilane, vinyltriethoxysilane, vinyltriacetoxysilane, and γ-glycidoxypropyltrimethoxysilane.

Examples of the organotitanium compounds include tetramethyl titanate, tetraisopropyl titanate, tetra-n-butyl titanate, butyl titanate dimer, and tetra(2-ethylhexyl) titanate.

Examples of the organozirconium compounds include zirconium isopropoxide, zirconium n-butoxide, zirconium acetylacetonate, and zirconyl acetate.

Examples of the organoaluminum compounds include aluminum acetylacetonate and a chelate compound of a salt of aluminum and an organic acid.

Examples of the acidic group-containing organic compound containing a phosphate group include: 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, and bis[2-(meth)acryloyloxy-(1-hydroxymethyl)ethyl]hydrogen phosphate; and their acid chlorides, alkali metal salts, and ammonium salts.

Examples of compounds which can be suitably used as the acidic group-containing organic compound having an acidic group such as a pyrophosphate group, a thiophosphate group, a phosphonate group, a sulfonate group, a carboxylate group or the like include those disclosed in WO 2012/042911 A1.

One of the above surface treatment agents may be used alone or two or more thereof may be used in combination. In order to enhance the chemical bonding between the inorganic filler and the polymerizable monomer and thereby increase the mechanical strength of the cured product, it is more preferable to use a surface treatment agent having a functional group copolymerizable with the polymerizable monomer.

The amount of the surface treatment agent used is not particularly limited, and is preferably 0.1 to 50 parts by weight per 100 parts by weight of the inorganic filler.

When the dental curable composition is used, for example, as a quick cure resin, an organic filler may be used as the filler (c) as well as the above inorganic filler. Examples of the organic filler include particles of polymethyl methacrylate, polyethyl methacrylate, methyl methacrylate-ethyl methacrylate copolymer, crosslinked polymethyl methacrylate, crosslinked polyethyl methacrylate, polyamide, polyvinyl chloride, polystyrene, chloroprene rubber, nitrile rubber, ethylene-vinyl acetate copolymer, styrene-butadiene copolymer, acrylonitrile-styrene copolymer, and acrylonitrile-styrene-butadiene copolymer. These fillers can be used alone or in the form of a mixture of two or more thereof. The shape of the particles of the organic filler is not particularly limited, and the particle diameter of the filler can be selected as appropriate.

When the dental curable composition is used as an adhesive or a resin cement, the curable component further contains an acidic group-containing polymerizable monomer (d) that is an adhesive monomer, in addition to the polymerizable monomer (a) having no acidic group and the polymerization initiator (b). The acidic group-containing polymerizable monomer (d) is a component contributing to improvement in adhesive properties to a tooth structure and a dental prosthesis. Examples of such a polymerizable monomer include polymerizable monomers having at least one acidic group such as a phosphate group, a phosphonate group, a pyrophosphate group, a carboxylate group, a sulfonate group, or a thiophosphate group and having a polymerizable unsaturated group such as an acryloyl group, a methacryloyl group, a vinyl group, or a styrene group. Specific examples of such compounds are mentioned below.

Examples of the phosphate group-containing polymerizable monomer include: polymerizable monomers such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl-2-dihydrogen phosphate, 2-(meth)acryloyloxyethylphenyl hydrogen phosphate, 2-(meth)acryloyloxyethyl-2'-bromoethyl hydrogen phosphate, 2-methacryloyloxyethyl(4-methoxyphenyl) hydrogen phosphate, 2-methacryloyloxypropyl(4-methoxyphenyl) hydrogen phosphate, glycerol phosphate di(meth)acrylate, and dipentaerythritol phosphate penta(meth)acrylate; and acid chlorides thereof.

Examples of the phosphonate group-containing polymerizable monomer include: polymerizable monomers such as 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, and 10-(meth)acryloyloxydecyl-3-phosphonoacetate, and acid chlorides thereof.

Examples of the pyrophosphate group-containing polymerizable monomer include: polymerizable monomers such as bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, and bis[10-(meth)acryloyloxydecyl]pyrophosphate; and acid chlorides thereof.

Examples of the carboxylate group-containing polymerizable monomer include: polymerizable monomers such as maleic acid, methacrylic acid, 4-[2-[(meth)acryloyloxy]ethoxycarbonyl]phthalic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, acid anhydrides thereof, 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, and 11-(meth)acryloyloxy-1,1-undecanedicarboxylic acid; and acid chlorides thereof.

Examples of the sulfonate group-containing polymerizable monomer include: polymerizable monomers such as 2-(meth)acrylamido-2-methylpropanesulfonic acid, styrenesulfonic acid, and 2-sulfoethyl (meth)acrylate; and acid chlorides thereof.

Examples of the thiophosphate group-containing polymerizable monomer include: polymerizable monomers such as 10-(meth)acryloyloxydecyl dihydrogen dithiophosphate; and acid chlorides thereof.

Among these acidic group-containing polymerizable monomers (d), a polymerizable monomer having a phosphate group or a thiophosphate group is preferably used in terms of good adhesive properties to a tooth structure and a dental prosthesis. Particularly, a divalent phosphate group-containing polymerizable monomer whose molecule has an alkyl group or an alkylene group having a main chain containing 6 to 20 carbon atoms is more preferable. Most preferred is a divalent phosphate group-containing polymerizable monomer, such as 10-methacryloyloxydecyl dihydrogen phosphate, whose molecule has an alkylene group having a main chain containing 8 to 12 carbon atoms.

One type of the acidic group-containing polymerizable monomer (d) may be contained alone or a combination of two or more types of the acidic group-containing polymerizable monomers (d) may be contained.

When used as an adhesive or a resin cement, particularly when used as a resin cement, the dental curable composition contains a filler (c) which is the same as that used in a composite resin.

When the dental curable composition is used as a glass ionomer cement, the glass ionomer cement includes, as an essential component, a curable component including a polyalkenoic acid (e), an ion-leachable glass (f), and water (g). The glass ionomer cement undergoes curing reaction induced by the fact that the carboxylate group of the polyalkenoic acid is ionically bonded via the water to the cationic component of the ion-leachable glass filler to form a polysalt.

The polyalkenoic acid (e) used in the present invention is an organic polymer that has, as a component involved in glass ionomer reaction, a carboxyl group or another acidic group capable of reacting with the cation leached from the ion-leachable glass (f) to form a polysalt. The polyalkenoic acid (e) contributes to exhibition of adhesive properties to a tooth structure and a dental prosthesis. The polyalkenoic acid (e) is preferably a (co)polymer of an unsaturated carboxylic acid such as an unsaturated monocarboxylic acid or an unsaturated dicarboxylic acid, and examples of the (co)polymer include homopolymers of acrylic acid, methacrylic acid, 2-chloroacrylic acid, 2-cyanoacrylic acid, aconitic acid, mesaconic acid, maleic acid, itaconic acid, fumaric acid, glutaconic acid, citraconic acid, and the like; copolymers of two or more of these unsaturated carboxylic acids; and copolymers of these unsaturated carboxylic acids with other monomers copolymerizable with the unsaturated carboxylic acids. These polymers may be used alone or two or more thereof may be used in combination. In the case of a copolymer of any of the unsaturated carboxylic acids with another copolymerizable monomer, the proportion of the unsaturated carboxylic acid unit is preferably 50 mol % or more in the total structural units. The copolymerizable monomer is preferably an ethylenically unsaturated polymerizable monomer, and examples thereof include styrene, acrylamide, acrylonitrile, methyl methacrylate, acrylic acid salts, vinyl chloride, allyl chloride, vinyl acetate, and 1,1,6-trimethylhexamethylene dimethacrylate. Among these polyalkenoic acids, at least one selected from the group consisting of homopolymers of acrylic acid, maleic acid, and itaconic acid, a copolymer of acrylic acid with maleic acid, and a copolymer of acrylic acid with itaconic acid is preferable, and the copolymer of acrylic acid with itaconic acid is particularly preferable, in terms of improvement in bond strength to a tooth structure and in mechanical strength. Additionally, a polymer containing no polymerizable ethylenically unsaturated double bond and having a weight-average molecular weight of 5,000 to 50,000 is preferable. If the weight-average molecular weight is less than 5,000, the strength of the resulting cured product is likely to be low, and bond strength to a tooth structure may be reduced; therefore, the weight-average molecular weight is more preferably 10,000 or more, and most preferably 35,000 or more. If the weight-average molecular weight is more than 50,000, the handling properties may be reduced; therefore, the weight-average molecular is more preferably 45,000 or less, and most preferably 40,000 or less.

The method for producing the polyalkenoic acid (e) used in the present invention is not particularly limited. When a commercialized product is available, it may be used. Particularly, when the polyalkenoic acid (e) is contained in powder form, it is often preferable to further pulverize a commercialized product. In doing so, a pulverizer such as a ball mill, a grinder, or a jet mill can be used. Alternatively, the polyalkenoic acid (e) may be obtained by pulverizing a polyalkenoic acid powder together with a liquid medium such as an alcohol using a grinder, a ball mill, or the like to prepare a slurry and then by drying the obtained slurry. A dryer used in this case is preferably a spray dryer.

The ion-leachable glass (f) refers to glass from which is leached a cation having a valence of two or more and capable of reacting with the polyalkenoic acid (e), such as an ion of strontium, calcium, zinc, aluminum, iron, or zirconium. Specific examples of the glass include fluoroaluminosilicate glass, calcium fluoroaluminosilicate glass, strontium fluoroaluminosilicate glass, barium fluoroaluminosilicate glass, and strontium calcium fluoroaluminosilicate glass. Among these, fluoroaluminosilicate glass and barium fluoroaluminosilicate glass are preferable. One type of the ion-leachable glass (f) may be used or two or more types of the ion-leachable glasses (f) may be used in combination where appropriate.

The method for producing the ion-leachable glass (f) used in the present invention is not particularly limited. Generally, the ion-leachable glass (f) can be produced by weighing materials at a given weight ratio, mixing the materials well, then melting the mixture at a high temperature of not less than 1100° C., quickly cooling the homogeneous molten body into a glass frit, and pulverizing the glass frit using a common pulverization means, such as a ball mill, a grinder, or a jet mill. Alternatively, a commercially-available ion-leachable glass powder may be used as such or may be further pulverized. The average particle diameter of the ion-leachable glass (f) is preferably 0.02 to 35 µm. The ion-leachable glass (f) having an average diameter of less than 0.02 µm is difficult to produce due to the too small average particle diameter, and may cause too high a viscosity of the resulting dental curable composition. The average particle diameter of the ion-leachable glass (f) is more preferably 0.5 µm or more, and most preferably 1 µm or more. If, however, the average particle diameter of the ion-leachable glass (f) is more than 35 µm, the surface of the resulting dental curable composition may be rough and coarse or its handling properties may be reduced. The average particle diameter of the ion-leachable glass (f) is more preferably 20 µm or less, and most preferably 10 µm or less. The average particle diameter of the ion-leachable glass (f) used in the present invention is determined as a median diameter (d50) measured with a laser diffraction particle size distribution analyzer.

Where necessary, the ion-leachable glass (f) may, similar to the filler (c), be surface-treated before use with a commonly-known surface treatment agent such as a silane coupling agent.

Additionally, there may be used compounds, such as tartaric acid serving as a curing time modifier for glass ionomer cements, which are commonly known as components of conventional glass ionomer cements.

When the dental curable composition is used as a resin-modified glass ionomer cement, the resin-modified glass ionomer cement includes, as an essential component, a curable component including the polymerizable monomer (a) having no acidic group, the polymerization initiator (b), the polyalkenoic acid (e), the ion-leachable glass (f), and the water (g). The resin-modified glass ionomer cement undergoes curing induced by curing reaction involving the polymerizable monomer (a) having no acidic group and the polymerization initiator (b) and curing reaction involving the polyalkenoic acid (e) and the ion-leachable glass (f).

Additionally, there may be used compounds, such as tartaric acid serving as a curing time modifier for resin-modified glass ionomer cements, which are commonly known as components of conventional resin-modified glass ionomer cements.

When the dental curable composition of the present invention is used as a resin-modified glass ionomer cement, the curable component may further contain the acidic group-containing polymerizable monomer (d), which is an adhesive monomer, particularly for the purpose of enhancing adhesive properties.

In order to be endowed with fluorine ion release ability, the dental curable composition according to the present invention can further contain a commonly-known water-soluble fluoride compound or fluorine-releasing polymer to the extent that the function of the dental curable composition is not adversely affected. Examples of the water-soluble fluoride compound include water-soluble metal fluorides such as lithium fluoride, sodium fluoride, potassium fluoride, rubidium fluoride, cesium fluoride, beryllium fluoride, magnesium fluoride, calcium fluoride, strontium fluoride, barium fluoride, zinc fluoride, aluminum fluoride, manganese fluoride, copper fluoride, lead fluoride, silver fluoride, antimony fluoride, cobalt fluoride, bismuth fluoride, tin fluoride, diammine silver fluoride, sodium monofluorophosphate, potassium fluorotitanate, fluorostannate, and fluorosilicate. One or more of these fluorides may be used. A method preferably used for allowing the metal fluoride to be contained is, for example, microparticulation of the metal fluoride or coating of the metal fluoride with polysiloxane.

As the fluorine-releasing polymer, there can be used compounds disclosed in JP 57-88106 A.

Also, in order to enhance the calcium ion release ability, the dental curable composition according to the present invention can further contain a commonly-known inorganic calcium compound to the extent that the function of the dental curable composition is not adversely affected.

Examples of the inorganic calcium compound include acidic calcium phosphate particles, basic calcium phosphate particles, and calcium compounds containing no phosphorus. The acidic calcium phosphate particles are not particularly limited, and are preferably at least one type of particles selected from the group consisting of anhydrous calcium hydrogen phosphate [$CaHPO_4$] particles, tricalcium phosphate [$Ca_3(PO_4)_2$] particles, anhydrous calcium dihydrogen phosphate [$Ca(H_2PO_4)_2$] particles, amorphous calcium phosphate [$Ca_3(PO_4)_2 \cdot xH_2O$] particles, acidic calcium pyrophosphate [$CaH_2P_2O_7$] particles, calcium hydrogen phosphate dihydrate [$CaHPO_4 \cdot 2H_2O$] particles, and calcium dihydrogen phosphate monohydrate [$Ca(H_2PO_4)_2 \cdot H_2O$] particles. Among these, at least one type of particles selected from the group consisting of anhydrous calcium hydrogen phosphate [$CaHPO_4$] particles, tricalcium phosphate [$Ca_3(PO_4)_2$] particles, anhydrous calcium dihydrogen phosphate [$Ca(H_2PO_4)_2$] particles, and calcium hydrogen phosphate dihydrate [$CaHPO_4 \cdot 2H_2O$] particles, are more suitably used. Even more suitably used are at least one type of particles selected from the group consisting of anhydrous calcium hydrogen phosphate [$CaHPO_4$] particles and calcium hydrogen phosphate dihydrate [$CaHPO_4 \cdot 2H_2O$] particles. Particularly in terms of calcium ion release ability, anhydrous calcium hydrogen phosphate [$CaHPO_4$] particles are suitably used.

The basic calcium phosphate particles are not particularly limited either, and are preferably at least one type of particles selected from the group consisting of tetracalcium phosphate [$Ca_4(PO_4)_2O$] particles and octacalcium phosphate pentahydrate [$Ca_8H_2(PO_4)_6 \cdot 5H_2O$] particles. Among these, tetracalcium phosphate [$Ca_4(PO_4)_2O$] particles are more suitably used particularly in terms of calcium ion release ability.

The calcium compounds containing no phosphorus are not particularly limited either. Examples thereof include calcium hydroxide [$Ca(OH)_2$], calcium oxide [$CaO$], calcium chloride [$CaCl_2$], calcium nitrate [$Ca(NO_3)_2 \cdot nH_2O$], calcium acetate [$Ca(CH_3CO_2)_2 \cdot nH_2O$], calcium lactate [$C_6H_{10}CaO_6$], calcium citrate [$Ca_3(C_6H_5O_7)_2 \cdot nH_2O$], calcium metasilicate [$CaSiO_3$], dicalcium silicate [$Ca_2SiO_4$], tricalcium silicate [$Ca_3SiO_5$], and calcium carbonate [$CaCO_3$], and one or more of these compounds are used. Among these, calcium hydroxide, calcium oxide, calcium metasilicate, dicalcium silicate, and tricalcium silicate are preferable, and calcium hydroxide is more preferable, in terms of precipitation yield of a hydroxyapatite component.

The dental curable composition of the present invention may further contain a stabilizer (polymerization inhibitor), a colorant, a fluorescent agent, and an ultraviolet absorber. Furthermore, there may be added an antibacterial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, or triclosan.

When the dental curable composition of the present invention is used as a resin material, that is, a dental composite resin, a dental adhesive, a dental resin cement, or a dental quick cure resin, its essential components are: the sugar compound having the —XM group; and a curable component including the polymerizable monomer (a) having no acidic group and the polymerization initiator (b). As regards the content ratio in the curable component, 0.01 to 15 parts by weight of the polymerization initiator (b) is generally used per 100 parts by weight of the polymerizable monomer (a) having no acidic group. The composition is converted to a cured product through curing reaction induced by the fact that an active species such as a radical produced from the polymerization initiator (b) binds to a double bond of the polymerizable monomer through an addition reaction. If the content of the polymerization initiator (b) is too low, the curing reaction does not proceed sufficiently, with the result that the physical properties of the cured product are likely to be insufficient, while if its content is too high, the polymerization initiator (b) is present as a foreign matter in the cured product, also with the result that the physical properties of the cured product are likely to be insufficient. In view of these facts and also in view of obtaining a curing reaction rate which is appropriate in terms of the handling properties of the composition, the content of the polymerization initiator (b) is preferably in the range of 0.05 to 10 parts by weight and more preferably in the range of 0.1 to 7 parts by weight.

When the dental curable composition is used as a composite resin, the dental curable composition further contains the filler (c), in addition to the sugar compound having the —XM group, the polymerizable monomer (a) having no acidic group, and the polymerization initiator (b). In this case, the filler (c) is used generally in an amount of 1 to 2000 parts by weight per 100 parts by weight of the polymerizable monomer (a) having no acidic group. If the content of the filler (c) is too low, a sufficient effect of adding the filler (c) on improvement in the physical properties of the cured product is less likely to be obtained, while if the content is too high, the composition has too high a viscosity and is difficult to handle. Therefore, the content of the filler (c) is preferably in the range of 2 to 1500 parts by weight and more preferably in the range of 5 to 1000 parts by weight.

The resin material may further contain the acidic group-containing polymerizable monomer (d) so as to be endowed with an adhesive function. The acidic group-containing polymerizable monomer (d) is generally used in an amount of 1 to 100 parts by weight per 100 parts by weight of the polymerizable monomer (a) having no acidic group. If the content of the acidic group-containing polymerizable monomer (d) is too low, exertion of a desired adhesive function is likely to be insufficient, while if the content is too high, the curing reaction is inhibited due to acidity, with the result that the physical properties of the cured product are likely to be insufficient and that a sufficient adhesive function is less likely to be exerted. Therefore, the content of the acidic group-containing polymerizable monomer (d) is preferably in the range of 2 to 70 parts by weight and more preferably in the range of 5 to 50 parts by weight.

When the dental curable composition of the present invention is used as a glass ionomer cement, its essential components are: the sugar compound having the —XM group; and a curable component including the polyalkenoic acid (e), the ion-leachable glass (f), and the water (g). As regards the content ratio in the curable component, generally, 100 to 2000 parts by weight of the ion-leachable glass (f) and 50 to 400 parts by weight of the water (g) are used per 100 parts by weight of the polyalkenoic acid (e). In order to obtain an appropriate level of physical properties of the cured product and obtain an appropriate level of handling properties dependent on curing reaction during mixing, the content of the ion-leachable glass (f) is preferably in the range of 200 to 1500 parts by weight and more preferably in the range of 500 to 1000 parts by weight. Also, the content of the water (g) is preferably in the range of 70 to 300 parts by weight and more preferably in the range of 100 to 200 parts by weight.

When the dental curable composition of the present invention is used as a resin-modified glass ionomer cement, its essential components are: the sugar compound having the —XM group; and a curable component including the polymerizable monomer (a) having no acidic group, the polymerization initiator (b), the polyalkenoic acid (e), the ion-leachable glass (f), and the water (g). As regards the content ratio in the curable component, generally, 0.01 to 15 parts by weight of the polymerization initiator (b), 1 to 1200 parts by weight of the polyalkenoic acid (e), 100 to 2000 parts by weight of the ion-leachable glass (f), and 0.5 to 200 parts by weight of the water (g) are used per 100 parts by weight of the polymerizable monomer (a) having no acidic group. In order to obtain a desired level of physical properties of the cured product and obtain an appropriate level of handling properties dependent on curing reaction during mixing, the content of the polymerization initiator (b) is preferably in the range of 0.05 to 10 parts by weight and more preferably in the range of 0.1 to 7 parts by weight. The content of the polyalkenoic acid (e) is preferably in the range of 2 to 1000 parts by weight and more preferably in the range of 5 to 700 parts by weight. The content of the ion-leachable glass (f) is preferably in the range of 200 to 1500 parts by weight and more preferably in the range of 500 to 1000 parts by weight. The content of the water (g) is preferably in the range of 1 to 150 parts by weight and more preferably in the range of 2 to 100 parts by weight.

The forms of the dental curable composition of the present invention provided for dental treatment are classified according to the curing mode of the composition.

When the dental curable composition is of the one-paste type, it is provided in a form in which the sugar compound having the —XM group is dispersed in the paste or dissolved in the polymerizable monomer.

When the dental curable composition is of the two-paste mixing type, it is provided in a form in which the sugar compound having the —XM group is dispersed in one or both of the pastes or dissolved in the polymerizable monomer.

When the dental curable composition is of the powder-liquid mixing type, it is provided in a form in which the sugar compound having the —XM group is dispersed in the powder material and/or dispersed or dissolved in the liquid material. When the curable component includes the polyalkenoic acid (e), the ion-leachable glass (f), and the water (g), it is preferable, regardless of the form of the composition, that the three components, the polyalkenoic acid (e), the ion-leachable glass (f), and the water (g), not be present together in either one of the powder and liquid materials.

The cured product of the dental curable composition of the present invention has high metal ion release ability and also has highly durable physical properties. Particularly, despite releasing metal ions, the cured product has highly durable adhesive properties to a tooth structure and a dental prosthesis, and can maintain a high level of mechanical strength over a long period of time. The dental curable composition of the present invention can be composed to release metal ions useful, for example, for prevention of caries by tooth structure strengthening and for repair of early caries. That is, the dental curable composition of the present invention, when cured, has high metal ion release ability and is not subject to deterioration in physical properties associated with metal ion release; therefore, the dental curable composition can contribute to maintaining the oral function involving a restorative material over a long period of time.

The usage of the dental curable composition of the present invention does not differ from those of dental restorative materials which are generally commercially available. The dental curable composition of the present invention is provided for various applications such as a dental restorative filling material, a dental adhesive material, a dental luting material, a dental temporary sealing material, a dental provisional crown material, and a dental pit and fissure sealant. The dental curable composition of the present invention is used for dental treatment according to an ordinary method.

When the dental curable composition of the present invention is used as a dental adhesive material, it can be used as a restorative material not only for a tooth structure but also for a crown restoration material (made of metal, porcelain, ceramic, cured composite, or the like) fractured in an oral cavity. Since pieces of the crown restoration material are adhered together, the effect of metal ion release is not displayed at the adhered part. However, it is expected that metal ions leached into the oral cavity are adsorbed and incorporated in the surfaces of other teeth and thus provide the strengthening effect on the teeth in the entire oral cavity.

When the dental curable composition according to present invention is used in adhesion of a crown restoration material, the dental curable composition of the present invention may be used in combination with a primer such as a commercially-available primer for metal adhesion or porcelain adhesion or in combination with a tooth cleaning agent such as a hypochlorite or a hydrogen peroxide solution.

EXAMPLES

Hereinafter, the present invention will be described in more detail by way of examples. However, the present invention is not limited by the examples given below.

Production Example 1 (Production of Calcium Mannan Phosphate)

Mannan phosphate was synthesized according to the method of Production Example 2 of WO 2009/091001 A1. The specific procedures are as follows.

Using a separable flask with an inner volume of 2 L, 40.0 g of mannan (RHEOLEX LM manufactured by Shimizu Chemical Corporation) was dissolved in 200 mL of distilled water at room temperature. While the resulting solution was stirred, 1000 g of a 1M aqueous phosphoric acid solution (whose pH was adjusted to 5.5 with sodium hydroxide) was added to the solution over 10 minutes. After the addition, the stirring was continued for additional 1 hour. Thereafter, about 1100 mL of distilled water was distilled off at temperatures between 100° C. and 103° C., which was followed by continuous stirring at 170° C. for 3 hours and then by cooling of the reaction product to room temperature. The reaction product was taken out, and pulverized with a mortar to obtain a brown solid.

The thus obtained brown solid weighing 90 g was dissolved in 1500 mL of distilled water. While the resulting solution was stirred, 1500 mL of 99.5% ethanol was added to the solution over 10 minutes. Immediately after the start of the addition, formation of a deposit was observed. After the completion of addition, the stirring was continued for additional 1 hour. Thereafter, the solution was allowed to stand until the solution was separated into layers, and then the supernatant was removed by decantation. This was followed by further dissolution of the remaining precipitate in 1500 mL of distilled water, to which 1500 mL of 99.5% ethanol was added over 10 minutes, after which the resulting precipitate was collected. The above procedures were repeated twice, then the finally obtained precipitate was dissolved in distilled water (400 mL), and the resulting solution was added little by little to stirred 99.5% ethanol (2000 mL) over 5 minutes. The deposited precipitate was collected by filtration with a Hirsch funnel (3 G), washed with 99.5% ethanol (500 mL), and then dried under reduced pressure at 60° C. for 12 hours, yielding a white solid that was slightly brownish. Furthermore, 25 g of this white solid was dissolved in distilled water, and the resulting solution was processed by a small desktop electrodialyzer (Micro Acilyzer S3, manufactured by SUNACTIS CO., LTD.), so that 13 g of mannan phosphate was obtained in the form of a transparent, light-brown solid.

The solid thus obtained was subjected to IR analysis (by KBr pellet technique using FTIR-8200PC manufactured by Shimadzu Corporation). The result was that a peak attributed to a phosphate group moiety was observed in the region from 1000 to 1200 $cm^{-1}$. In addition, $^{31}$P-NMR was measured (with JNM-LA500 manufactured by JEOL Ltd.). The result was that a signal attributed to phosphorous linked to mannan via a phosphoester bond was detected in the region from 2 to 5 ppm. Element analysis on phosphorus atoms was performed by ICP emission spectroscopy (with IRIS-AP manufactured by Jarrell-Ash Co., Ltd.). From the result, it was determined that about 2.3% of the hydroxyl groups of mannan were phosphorylated. Furthermore, GPC analysis (column: TSKgel α-M (manufactured by Tosoh Corporation), mobile phase: 0.1 M aqueous NaCl solution) was performed, as a result of which the number average molecular weight (Mn) was determined to be 13,000. The phosphate groups of the mannan phosphate were neutralized with calcium hydroxide using water as a solvent, and the water was then distilled off. Thus, calcium mannan phosphate was obtained.

Production Example 2 (Production of Calcium Maltodextrin Phosphate)

Maltodextrin phosphate was synthesized according to the method of Production Example 3 of WO 2009/091001 A1. The specific procedures are as follows.

Maltodextrin phosphate was synthesized in the same manner as in Production Example 1 above, except that maltodextrin (Pinedex-2, manufactured by Matsutani Chemical Industry Co., Ltd.) was used as a raw material instead of mannan. About 2.8% of the hydroxyl groups of the maltodextrin were phosphorylated, and the number average molecular weight (Mn) of the maltodextrin phosphate was 1,400.

The phosphate groups of the maltodextrin phosphate were neutralized with calcium hydroxide using water as a solvent, and the water was then distilled off. Thus, calcium maltodextrin phosphate was obtained.

Production Example 3 (Production of Aluminum Carboxymethyl Cellulose)

An aqueous solution of aluminum nitrate was added to an aqueous solution of sodium carboxymethyl cellulose (manufactured by Tokyo Chemical Industry Co., Ltd.), and the mixed solution was stirred well. The resulting precipitate was collected and dried to obtain aluminum carboxymethyl cellulose.

Examples 1-1 to 1-14

Composite resin compositions shown in Tables 1-1 to 1-3, which were prepared by use of the raw materials listed below, were evaluated for their calcium ion release ability and flexural strength by employing the testing methods described later.

<Polymerizable Monomer (a)>
Bis-GMA: 2,2-bis[4-(3-methacryloyloxy-2-hydroxypropoxy)phenyl]propane
TEGDMA: Triethylene glycol dimethacrylate
D-2.6E: 2,2-bis(4-methacryloyloxypolyethoxyphenyl)propane (the average number of moles of added ethoxy groups: 2.6)
UDMA: 2,2,4-trimethylhexamethylenebis(2-carbamoyloxyethyl) dimethacrylate
HD: 1,6-hexanediol dimethacrylate
<Polymerization Initiator (b)>
CQ: dl-camphorquinone
TPO: 2,4,6-trimethylbenzoyldiphenylphosphine oxide
<Polymerization Accelerator>
DABE: Ethyl 4-(N,N-dimethylamino)benzoate
<Filler (c)>
Filler (c-1): Silane-treated Ba glass (GM27884 UF1.0 manufactured by SHOTT AG, Average particle diameter=1 μm, Silane concentration for treatment=3.2%)
<Another Component: Stabilizer (Polymerization Inhibitor)>
BHT: 2,6-di-t-butyl-4-methylphenol
<Sugar Compound Having —XM Group>
POs-Ca: Phosphoryl oligosaccharides of calcium (POs-Ca (registered trademark) 50, manufactured by GLICO NUTRITION CO., LTD.)
Calcium mannan phosphate: The calcium mannan phosphate produced in Production Example 1 was used.
Calcium maltodextrin phosphate: The calcium maltodextrin phosphate produced in Production Example 2 was used.
Aluminum carboxymethyl cellulose: The aluminum carboxymethyl cellulose produced in Production Example 3 was used.
<Sugar Compound Having No —XM Group>
Carboxymethyl cellulose: H-CMC manufactured by Daicel FineChem Ltd. was used.

[Method for Measuring Calcium Ion Release Ability of Composite Resin Composition]

Each composite resin composition was loaded into a stainless steel mold (with an inner diameter of 15 mm and a thickness of 1 mm). The composition was pressed between glass slides placed on its upper and lower surfaces, and each of the two surfaces was irradiated with light using a dental light irradiation unit (Pencure 2000, manufactured by Morita Corporation) at eight points for 20 seconds per point. The cured product was removed from the mold, and immersed in 5 ml of ion-exchange water (37° C.). After 28-day immersion, 5 ml of KCl (15 g/L) was added, and calcium ions leached into the ion-exchange water were quantified using a calcium ion electrode (manufactured by HORIBA, Ltd.).

[Method for Measuring Aluminum Ion Release Ability of Composite Resin Composition]

Each composite resin composition was loaded into a stainless steel mold (with an inner diameter of 15 mm and a thickness of 1 mm). The composition was pressed between glass slides placed on its upper and lower surfaces, and each of the two surfaces was irradiated with light using a dental light irradiation unit (Pencure 2000, manufactured by Morita Corporation) at eight points for 20 seconds per point. The cured product was removed from the mold, and immersed in 5 ml of ion-exchange water (37° C.). After 28-day immersion, aluminum ions leached into the ion-exchange water were quantitatively analyzed using an atomic absorption spectrophotometer (manufactured by Hitachi, Ltd.).

[Method for Measuring Flexural Strength of Composite Resin Composition]

Each composite resin composition was loaded into a stainless steel mold (with inner dimensions of 2 mm×2 mm×20 mm). The composition was pressed between glass slides placed on its upper and lower surfaces, and each of the two surfaces was irradiated with light using a dental light irradiation unit (Pencure 2000, manufactured by Morita Corporation) at five points for 20 seconds per point. Ten cured products were thus prepared, and were stored in 37° C. distilled water for 24 hours after removal from the mold. Five of the cured products were subjected to measurement first. For the measurement, a universal testing machine (Autograph, manufactured by Shimadzu Corporation) was used. The span was set to 20 mm, and the crosshead speed was set to 1 mm/min. An average of the measured values was determined as the initial value of the flexural strength of the sample. The other five cured products were stored in 70° C. distilled water for additional 10 days, and then subjected to measurement, so that an index of the durability of the flexural strength was determined.

Comparative Examples 1-1 to 1-4

Composite resin compositions shown in Table 1-1 and Table 1-2 were evaluated for their calcium ion release ability and flexural strength in the same manner as in Examples 1-1 to 1-14.

TABLE 1-1

| | | | Example 1-1 | Example 1-2 | Example 1-3 | Example 1-4 | Example 1-5 | Comp. Example 1-1 | Comp. Example 1-2 | Comp. Example 1-3 |
|---|---|---|---|---|---|---|---|---|---|---|
| Raw materials | Polymerizable monomer (a) | Bis-GMA (parts by weight) | 21 | 21 | 21 | 31.5 | 21 | 21 | 21 | 21 |
| | | TEGDMA (parts by weight) | 9 | 9 | 9 | 13.5 | 9 | 9 | 9 | 9 |
| | Polymerization initiator (b) | CQ (parts by weight) | 0.09 | 0.09 | 0.09 | 0.07 | 0.09 | 0.09 | 0.09 | 0.09 |
| | Polymerization accelerator | DABE (parts by weight) | 0.3 | 0.3 | 0.3 | 0.15 | 0.3 | 0.3 | 0.3 | 0.3 |
| | Filler (c) | Filler (c-1) (parts by weight) | 70 | 70 | 70 | 55 | 70 | 70 | 70 | 70 |
| | Another component | BHT (parts by weight) | 0.015 | 0.015 | 0.015 | 0.0225 | 0.015 | 0.015 | 0.015 | 0.015 |
| | POs-Ca (parts by weight) | | 1 | 2 | 5 | 9 | 11 | — | — | — |
| | Calcium hydroxide (parts by weight) | | — | — | — | — | — | — | 2 | — |
| | Calcium chloride (parts by weight) | | — | — | — | — | — | — | — | 2 |
| Amount of released calcium ions (μg) | | | 41 | 78 | 208 | 386 | 412 | 0 | 23 | 121 |
| Flexural strength | Immediately after production (MPa) | | 92 | 91 | 93 | 84 | 87 | 96 | 89 | 88 |
| | After 10-day storage at 70° C. (MPa) | | 91 | 90 | 91 | 82 | 78 | 93 | 35 | 12 |

TABLE 1-2

| | | | Example 1-6 | Example 1-7 | Example 1-8 | Comp. Example 1-4 |
|---|---|---|---|---|---|---|
| Raw materials | Polymerizable monomer (a) | Bis-GMA (parts by weight) | 21 | 21 | 21 | 21 |
| | | TEGDMA (parts by weight) | 9 | 9 | 9 | 9 |
| | Polymerization initiator (b) | CQ (parts by weight) | 0.09 | 0.09 | 0.09 | 0.09 |
| | Polymerization accelerator | DABE (parts by weight) | 0.3 | 0.3 | 0.3 | 0.3 |
| | Filler (c) | Filler (c-1) (parts by weight) | 70 | 70 | 70 | 70 |
| | Another component | BHT (parts by weight) | 0.015 | 0.0225 | 0.015 | 0.015 |
| | Calcium mannan phosphate (parts by weight) | | 2 | — | — | — |
| | Calcium maltodextrin phosphate (parts by weight) | | — | 1 | — | — |
| | Aluminum carboxymethyl cellulose (parts by weight) | | — | — | 4 | — |
| | Carboxymethyl cellulose (parts by weight) | | — | — | — | 3 |
| Amount of released calcium ions (μg) | | | 62 | 34 | 0 | 0 |
| Amount of released aluminum ions (μg) | | | 0 | 0 | 116 | 0 |
| Flexural strength | Immediately after production (MPa) | | 91 | 91 | 89 | 90 |
| | After 10-day storage at 70° C. (MPa) | | 87 | 88 | 84 | 87 |

TABLE 1-3

|  |  |  | Example 1-9 | Example 1-10 | Example 1-11 | Example 1-12 | Example 1-13 | Example 1-14 |
|---|---|---|---|---|---|---|---|---|
| Raw materials | Polymerizable monomer (a) | Bis-GMA (parts by weight) | 28 | 17.5 | — | 15.5 | — | 10.5 |
|  |  | D-2.6E (parts by weight) | — | — | 28 | 15.5 | — | 10.5 |
|  |  | UDMA (parts by weight) | — | — | — | — | 17.5 | — |
|  |  | TEGDMA (parts by weight) | 12 | 7.5 | 12 | 14 | 7.5 | 4.5 |
|  |  | HD (parts by weight) | — | — | — | — | — | 4.5 |
|  | Polymerization initiator (b) | CQ (parts by weight) | 0.12 | 0.075 | 0.12 | 0.14 | 0.05 | 0.06 |
|  |  | TPO (parts by weight) | — | — | — | — | 0.025 | 0.06 |
|  | Polymerization accelerator | DABE (parts by weight) | 0.4 | 0.25 | 0.4 | 0.45 | 0.1 | 0.12 |
|  | Filler (c) | Filler (c-1) (parts by weight) | 60 | 75 | 60 | 55 | 75 | 70 |
|  | Another component | BHT (parts by weight) | 0.02 | 0.0125 | 0.02 | 0.0225 | 0.0225 | 0.015 |
|  |  | POs-Ca (parts by weight) | 4 | 3 | 4 | 2.5 | 3.5 | 3 |
| Amount of released calcium ions (μg) |  |  | 183 | 107 | 145 | 115 | 140 | 135 |
| Flexural strength | Immediately after production (MPa) |  | 89 | 113 | 86 | 87 | 107 | 90 |
|  | After 10-day storage at 70° C. (MPa) |  | 86 | 109 | 85 | 87 | 102 | 89 |

Examples 2-1 to 2-10

Dental adhesive compositions shown in Tables 2-1 to 2-3, which were prepared by use of the raw materials listed below, were evaluated for their calcium ion release ability and bond strength to dentin by employing the testing methods described later.

<Polymerizable Monomer (a)>
Bis-GMA: 2,2-bis[4-(3-methacryloyloxy-2-hydroxypropoxy)phenyl]propane
HEMA: 2-hydroxyethyl methacrylate
NPGDMA: Neopentyl glycol dimethacrylate
<Polymerization Initiator (b)>
CQ: dl-camphorquinone
TPO: 2,4,6-trimethylbenzoyldiphenylphosphine oxide
<Polymerization Accelerator>
DABE: Ethyl 4-(N,N-dimethylamino)benzoate
<Filler (c)>
Filler (c-2): "Aerosil R-972" manufactured by Nippon Aerosil Co., Ltd., Average particle diameter=16 nm
Filler (c-3): "Aerosil 380" manufactured by Nippon Aerosil Co., Ltd., Average particle diameter=7 nm
<Acidic Group-Containing Polymerizable Monomer (d)>
MDP: 10-methacryloyloxydecyl dihydrogen phosphate
4-META: 4-[2-(methacryloyloxy)ethoxycarbonyl]phthalic anhydride
<Another Component: Stabilizer (Polymerization Inhibitor)>
BHT: 2,6-di-t-butyl-4-methylphenol
<Sugar Compound Having —XM Group>
POs-Ca: Phosphoryl oligosaccharides of calcium (POs-Ca (registered trademark) 50, manufactured by GLICO NUTRITION CO., LTD.)
Calcium mannan phosphate: The calcium mannan phosphate produced in Production Example 1 was used.
Aluminum carboxymethyl cellulose: The aluminum carboxymethyl cellulose produced in Production Example 3 was used.
<Sugar Compound Having No —XM Group>
Carboxymethyl cellulose: H-CMC manufactured by Daicel FineChem Ltd. was used.

[Method for Measuring Calcium Ion Release Ability of Dental Adhesive Composition]

Each dental adhesive composition was loaded into a stainless steel mold (with an inner diameter of 15 mm and a thickness of 1 mm). The composition was pressed between glass slides placed on its upper and lower surfaces, and each of the two surfaces was irradiated with light using a dental light irradiation unit (Pencure 2000, manufactured by Morita Corporation) at eight points for 20 seconds per point. The cured product was removed from the mold, and immersed in 5 ml of ion-exchange water (37° C.). After 28-day immersion, 5 ml of KCl (15 g/L) was added, and calcium ions leached into the ion-exchange water were quantified using a calcium ion electrode (manufactured by HORIBA, Ltd.).

[Method for Measuring Aluminum Ion Release Ability of Dental Adhesive Composition]

Each dental adhesive composition was loaded into a stainless steel mold (with an inner diameter of 15 mm and a thickness of 1 mm). The composition was pressed between glass slides placed on its upper and lower surfaces, and each of the two surfaces was irradiated with light using a dental light irradiation unit (Pencure 2000, manufactured by Morita Corporation) at eight points for 20 seconds per point. The cured product was removed from the mold, and immersed in 5 ml of ion-exchange water (37° C.). After 28-day immersion, aluminum ions leached into the ion-exchange water were quantitatively analyzed using an atomic absorption spectrophotometer (manufactured by Hitachi, Ltd.).

[Method for Measuring Tensile Bond Strength of Dental Adhesive Composition to Dentin]

The labial surface of a bovine mandibular incisor was ground with #80 silicon carbide paper (manufactured by NIHON KENSHI CO., LTD.) under running water, and a sample with an exposed flat dentin surface was obtained. The sample obtained was further ground with #1000 silicon carbide paper (manufactured by NIHON KENSHI CO., LTD.) under running water. After the completion of grinding, the sample was dried by removing water from its surface by air-blowing. To the dried smooth surface was attached an about 150-μm-thick adhesive tape having a circular hole of 3-mm diameter, so that an adhesive area was delimited.

A primer for tooth structures, CLEARFIL MEGA BOND (manufactured by Kuraray Noritake Dental Inc.), was applied within the circular hole using a brush, and left for 20 seconds, after which the applied primer was dried by subjecting its surface to air-blowing until the primer lost its flowability. Next, the dental adhesive composition was applied over the tooth surface on which the primer was applied and dried. Subsequently, the applied primer and dental adhesive composition were cured by 10-second light irradiation using a dental light irradiation unit (manufactured by Morita Corporation under the trade name "Pencure 2000").

A dental filling composite resin (manufactured by Kuraray Noritake Dental Inc. under the trade name "CLEARFIL AP-X") was applied to the surface of the obtained cured product of the dental adhesive composition, and was covered with a release film (polyester). Next, a glass slide was placed on and pressed against the release film to flatten the surface of the applied composite resin. Subsequently, using the irradiation unit "Pencure 2000", the composite resin was irradiated with light through the release film for 20 seconds to cure the composite resin.

Using a commercially-available dental resin cement (manufactured by Kuraray Noritake Dental Inc. under the trade name "PANAVIA 21"), a cylindrical stainless steel rod (with a diameter of 7 mm and a length of 2.5 cm) was bonded at its one end face (circular end face) to the surface of the obtained cured product of the dental filling composite resin. Thus, a test specimen was prepared. A total of 16 such test specimens were prepared. Next, the test specimens immersed in distilled water held in a sample container were left in a thermostat set at 37° C. for 24 hours, after which eight of the specimens were taken out and measured for their bond strength. For the measurement of the bond strength (tensile bond strength), a universal testing machine (Autograph, manufactured by Shimadzu Corporation) was used, and the crosshead speed was set to 2 mm/min. An average of the measured values was determined as the initial value of the tensile bond strength to dentin.

The other eight specimens were subjected to thermal cycling in which they were immersed alternately in a 4° C. water bath and a 60° C. water bath for 1 minute each. After 4000 cycles of the thermal cycling, the tensile bond strength of each specimen was measured, and an average of the measured values was determined as an index of the durability of the tensile bond strength to dentin.

Comparative Examples 2-1 to 2-4

Dental adhesive compositions shown in Tables 2-1 to 2-2 were evaluated for their calcium ion release ability and tensile bond strength to dentin in the same manner as in Examples 2-1 to 2-10.

TABLE 2-1

| | | | Example 2-1 | Example 2-2 | Example 2-3 | Example 2-4 | Example 2-5 | Comp. Example 2-1 | Comp. Example 2-2 | Comp. Example 2-3 |
|---|---|---|---|---|---|---|---|---|---|---|
| Raw materials | Polymerizable monomer (a) | Bis-GMA (parts by weight) | 37 | 37 | 37 | 37 | 37 | 37 | 37 | 37 |
| | | HEMA (parts by weight) | 40 | 40 | 40 | 40 | 40 | 40 | 40 | 40 |
| | | NPGDMA (parts by weight) | 20 | 20 | 20 | 20 | 20 | 20 | 20 | 20 |
| | Polymerization initiator (b) | CQ (parts by weight) | 0.3 | 0.3 | 0.3 | 0.3 | 0.3 | 0.3 | 0.3 | 0.3 |
| | Polymerization accelerator | DABE | 2 | 2 | 2 | 2 | 2 | 2 | 2 | 2 |
| | Filler (c) | Filler (c-2) (parts by weight) | 6 | 6 | 6 | 6 | 6 | 6 | 6 | 6 |
| | | Filler (c-3) (parts by weight) | 1.5 | 1.5 | 1.5 | 1.5 | 1.5 | 1.5 | 1.5 | 1.5 |
| | Acidic group containing polymerizable monomer (d) | MDP (parts by weight) | 3 | 3 | 3 | 3 | 3 | 3 | 3 | 3 |
| | Another component | BHT (parts by weight) | 0.05 | 0.05 | 0.05 | 0.05 | 0.05 | 0.05 | 0.05 | 0.05 |
| | | POs-Ca (parts by weight) | 0.5 | 1.1 | 2 | 4 | 5.8 | — | — | — |
| | | Calcium hydroxide (parts by weight) | — | — | — | — | — | — | 0.5 | — |
| | | Calcium chloride (parts by weight) | — | — | — | — | — | — | — | 0.5 |
| Amount of released calcium ions (μg) | | | 69 | 138 | 253 | 501 | 683 | 0 | 16 | 85 |
| Bond strength to dentin | | Immediately after production (MPa) | 19 | 18 | 21 | 20 | 17 | 20 | 18 | 16 |
| | | After 4000 cycles of thermal cycling (MPa) | 18 | 17 | 19 | 18 | 15 | 17 | 12 | 0 |

TABLE 2-2

| | | | Example 2-6 | Example 2-7 | Comp. Example 2-4 |
|---|---|---|---|---|---|
| Raw materials | Polymerizable monomer (a) | Bis-GMA (parts by weight) | 37 | 37 | 37 |
| | | HEMA (parts by weight) | 40 | 40 | 40 |
| | | NPGDMA (parts by weight) | 20 | 20 | 20 |
| | Polymerization initiator (b) | CQ (parts by weight) | 0.3 | 0.3 | 0.3 |
| | Polymerization accelerator | DABE | 2 | 2 | 2 |
| | Filler (c) | Filler (c-2) (parts by weight) | 6 | 6 | 6 |
| | | Filler (c-3) (parts by weight) | 1.5 | 1.5 | 1.5 |
| | Acidic group-containing polymerizable monomer (d) | MDP (parts by weight) | 3 | 3 | 3 |
| | Another component | BHT (parts by weight) | 0.05 | 0.05 | 0.05 |
| | | Calcium mannan phosphate (parts by weight) | 1 | — | — |

TABLE 2-2-continued

|  |  | Example 2-6 | Example 2-7 | Comp. Example 2-4 |
|---|---|---|---|---|
| Aluminum carboxymethyl cellulose (parts by weight) | | — | 1 | — |
| Carboxymethyl cellulose (parts by weight) | | — | — | 0.5 |
| Amount of released calcium ions (μg) | | 126 | 0 | 0 |
| Amount of released aluminum ions (μg) | | 0 | 40 | 0 |
| Bond strength to dentin | Immediately after production (MPa) | 20 | 19 | 18 |
|  | After 4000 cycles of thermal cycling (MPa) | 19 | 18 | 16 |

TABLE 2-3

| | | | Example 2-8 | Example 2-9 | Example 2-10 |
|---|---|---|---|---|---|
| Raw materials | Polymerizable monomer (a) | Bis-GMA (parts by weight) | 37 | 37 | 37 |
| | | HEMA (parts by weight) | 40 | 40 | 40 |
| | | NPGDMA (parts by weight) | 20 | 20 | 20 |
| | Polymerization initiator (b) | CQ (parts by weight) | 0.3 | 0.3 | 0.1 |
| | | TPO | — | — | 3 |
| | Polymerization accelerator | DABE | 2 | 2 | 1 |
| | Filler (c) | Filler (c-2) (parts by weight) | 6 | — | 6 |
| | | Filler (c-3) (parts by weight) | 1.5 | — | 1.5 |
| | Acidic group-containing polymerizable monomer (d) | MDP (parts by weight) | 1.5 | 3 | 3 |
| | | 4-META (parts by weight) | 1.5 | — | — |
| | Another component | BHT (parts by weight) | 0.05 | 0.05 | 0.05 |
| | | POs-Ca (parts by weight) | 1 | 0.5 | 2 |
| Amount of released calcium ions (μg) | | | 133 | 78 | 268 |
| Bond strength to dentin | Immediately after production (MPa) | | 15 | 14 | 18 |
| | After 4000 cycles of thermal cycling (MPa) | | 15 | 13 | 16 |

Examples 3-1 to 3-5

Resin cement compositions shown in Table 3-1, which were prepared by use of the raw materials listed below, were evaluated for their calcium ion release ability, flexural strength, and tensile bond strength to zirconia using the testing methods described later.

<Polymerizable Monomer (a)>
D-2.6E: 2,2-bis(4-methacryloyloxypolyethoxyphenyl)propane (Average number of moles of added ethoxy groups=2.6)
NPGDMA: Neopentyl glycol dimethacrylate
801: 1,2-bis(3-methacryloyloxy-2-hydroxypropoxy)ethane <Polymerization Initiator (b)>
BPO: Benzoyl peroxide
CQ: dl-camphorquinone
DEPT: N, N-bis(2-hydroxyethyl)-p-toluidine <Polymerization Accelerator>
TPSS: Sodium 2,4,6-triisopropylbenzenesulfinate
DABS: Ethyl 4-(N,N-dimethylamino)benzoate <Filler (c)>
Filler (c-4): 3-methacryloyloxypropyltrimethoxysilane-treated silica powder Silica ("KE-P250" manufactured by NIPPON SHOKUBAI CO., LTD.) was pulverized with a vibrating ball mill to obtain silica powder. In a 500 mL one-necked eggplant flask were put 100 g of the obtained silica powder, 1.0 g (1.0 part by weight per 100 parts by weight of the filler) of 3-methacryloyloxypropyltrimethoxysilane ("KBM-503" manufactured by Shin-Etsu Silicones), and 200 mL of toluene, which were stirred together at room temperature for 2 hours. Subsequently, the toluene was distilled off under reduced pressure, followed by vacuum drying at 40° C. for 16 hours and then by vacuum drying at 90° C. for 3 hours. Thus, 3-methacryloyloxypropyltrimethoxysilane-treated silica powder (filler (c-4)) was obtained. The average particle diameter of the filler (c-4), as measured with a laser diffraction particle size distribution analyzer (manufactured by Shimadzu Corporation, Product code "SALD-2100"), was 2.5 μm.

Filler (c-5): Silane-treated fumed silica powder

In a 500 mL one-necked eggplant flask were put 100 g of fumed silica ("Aerosil OX50" manufactured by Nippon Aerosil Co., Ltd., Average particle diameter=40 nm), 7.0 g (7.0 parts by weight per 100 parts by weight of the filler) of 3-methacryloyloxypropyltrimethoxysilane ("KBM-503" manufactured by Shin-Etsu Silicones), and 200 mL of toluene, which were stirred together at room temperature for 2 hours. Subsequently, the toluene was distilled off under reduced pressure, followed by vacuum drying at 40° C. for 16 hours and then by vacuum drying at 90° C. for 3 hours. Thus, 3-methacryloyloxypropyltrimethoxysilane-treated fumed silica powder (filler (c-5)) was obtained.

Filler (c-6): Silane-treated Ba glass (GM27884 UF2.0 manufactured by SHOTT AG, Average particle diameter=2 μm, Silane concentration for treatment=1.0%)

<Acidic Group-Containing Polymerizable Monomer (d)>
MDP: 10-methacryloyloxydecyl dihydrogen phosphate <Another Component: Polymerization Inhibitor>
BHT: 2,6-di-t-butyl-4-methylphenol <Sugar Compound Having —XM Group>
POs-Ca: Phosphoryl oligosaccharides of calcium (POs-Ca (registered trademark) 50, manufactured by GLICO NUTRITION CO., LTD.)

[Method for Measuring Calcium Ion Release Ability of Resin Cement Composition]

Each resin cement composition was loaded into a stainless steel mold (with an inner diameter of 15 mm and a thickness of 1 mm). The composition was pressed between glass slides placed on its upper and lower surfaces, then allowed to stand in a thermostat set at 37° C. for 1 hour, and thereby cured. The cured product was removed from the mold, and immersed in 5 ml of ion-exchange water (37° C.). After 28-day immersion, 5 ml of KCl (15 g/L) was added, and calcium ions leached into the ion-exchange water were quantified using a calcium ion electrode (manufactured by HORIBA, Ltd.).

[Method for Measuring Flexural Strength of Resin Cement Composition]

Each resin cement composition was loaded into a stainless steel mold (with inner dimensions of 2 mm×2 mm×20 mm). The composition was pressed between glass slides placed on its upper and lower surfaces, then allowed to stand in a thermostat set at 37° C. for 1 hour, and thereby cured. Ten such cured products were prepared, and were stored in 37° C. distilled water for 24 hours after removal from the mold. Five of the cured products were subjected to measurement first. For the measurement, a universal testing machine (Autograph, manufactured by Shimadzu Corporation) was used. The span was set to 20 mm, and the crosshead speed was set to 1 mm/min. An average of the measured values was determined as the initial value of the flexural strength of the sample. The other five cured products were stored in 70° C. distilled water for additional 10 days, and then subjected to measurement, so that an index of the durability of the flexural strength was determined.

[Method for Measuring Tensile Bond Strength of Resin Cement Composition to Zirconia]

The surfaces of a sintered body of zirconia (manufactured by Kuraray Noritake Dental Inc. under the trade name "KATANA") having a parallelepiped shape (1 cm×1 cm×5 mm) were each ground with #1000 silicon carbide paper under running water to be flat and smooth, and were dried by removing water from the surfaces by air blowing. To the dried smooth surface was attached an about 150-μm-thick adhesive tape having a circular hole of 5-mm diameter, so that an adhesive area was delimited. Each resin cement composition (a paste obtained by mixing two types of pastes) was mounded on one end face (circular end face) of a cylindrical stainless steel rod (with a diameter of 7 mm and a length of 2.5 cm). The end face with the cement composition mounded thereon was placed on the smooth surface (adherend) within the circular hole in such a manner that the center of the circular hole and the center of the cylindrical stainless steel rod substantially coincided with each other. The cylindrical stainless steel rod was perpendicularly pressed against and bonded to the smooth surface, and thus a testing sample was prepared. There were prepared 14 such testing samples. An excess portion of the cement composition that spread out of the perimeter of the cylindrical stainless steel rod during the pressing was removed, then the testing samples were allowed to stand at room temperature for 30 minutes and immersed in distilled water. The testing samples immersed in distilled water were allowed to stand in a thermostat maintained at 37° C. for 24 hours, after which seven of the samples were examined for their tensile bond strength. The tensile bond strength was measured using a universal testing machine (Autograph, manufactured by Shimadzu Corporation) and setting the crosshead speed to 2 mm/min. An average of the measured values for the seven testing samples was determined as the initial value of the tensile bond strength to zirconia. The other seven samples were subjected to thermal cycling in which they were immersed alternately in a 4° C. water bath and a 60° C. water bath for 1 minute each. After 4000 cycles of the thermal cycling, the tensile bond strength of each sample was measured, and an average of the measured values was determined as an index of the durability of the tensile bond strength to zirconia.

Comparative Examples 3-1 to 3-3

Resin cement compositions shown in Table 3-2 were evaluated for their calcium ion release ability, flexural strength, and tensile bond strength to zirconia in the same manner as in Examples 3-1 to 3-5.

TABLE 3-1

| | | | Example 3-1 | | Example 3-2 | | Example 3-3 | | Example 3-4 | | Example 3-5 | |
|---|---|---|---|---|---|---|---|---|---|---|---|---|
| | | | Paste A | Paste B | Paste A | Paste B | Paste A | Paste B | Paste A | Paste B | Paste A | Paste B |
| Raw materials | Polymerizable monomer (a) | D-2.6E (parts by weight) | 55 | 45 | 55 | 45 | 55 | 45 | 55 | 45 | 55 | 45 |
| | | NPGDMA (parts by weight) | 25 | 35 | 25 | 35 | 25 | 35 | 25 | 35 | 25 | 35 |
| | | #801 (parts by weight) | — | 20 | — | 20 | — | 20 | — | 20 | — | 20 |
| | Polymerization initiator (b) | BPO (parts by weight) | 2.0 | — | 2.0 | — | 2.0 | — | 2.0 | — | 2.0 | — |
| | | CQ (parts by weight) | 0.25 | — | 0.25 | — | 0.25 | — | 0.25 | — | 0.25 | — |
| | Polymerization accelerator | DEPT (parts by weight) | — | 0.3 | — | 0.3 | — | 0.3 | — | 0.3 | — | 0.3 |
| | | TPSS (parts by weight) | — | 0.5 | — | 0.5 | — | 0.5 | — | 0.5 | — | 0.5 |
| | | DABE | — | 0.3 | — | 0.3 | — | 0.3 | — | 0.3 | — | 0.3 |
| | Filler (c) | Filler (c-4) (parts by weight) | 200 | — | 200 | — | 200 | — | 200 | — | 200 | — |
| | | Filler (c-5) (parts by weight) | 10 | 10 | 10 | 10 | 10 | 10 | 10 | 10 | 10 | 10 |
| | | Filler (c-6) (parts by weight) | — | 200 | — | 200 | — | 200 | — | 200 | — | 200 |
| | Acidic group containing polymerizable monomer (d) | MDP (parts by weight) | 20 | — | 20 | — | 20 | — | 20 | — | 20 | — |
| | Another component | BHT (parts by weight) | 0.05 | 0.05 | 0.05 | 0.05 | 0.05 | 0.05 | 0.05 | 0.05 | 0.05 | 0.05 |

TABLE 3-1-continued

|  |  | Example 3-1 | | Example 3-2 | | Example 3-3 | | Example 3-4 | | Example 3-5 | |
|---|---|---|---|---|---|---|---|---|---|---|---|
|  |  | Paste A | Paste B | Paste A | Paste B | Paste A | Paste B | Paste A | Paste B | Paste A | Paste B |
| POs-Ca (parts by weight) | | — | 1 | — | 2 | — | 5 | — | 10 | — | 20 |
| Calcium hydroxide (parts by weight) | | | | | | | | | | | |
| Calcium chloride (parts by weight) | | | | | | | | | | | |
| Weight ratio of Paste A/Paste B | | 1.0 | | 1.0 | | 1.0 | | 1.0 | | 1.0 | |
| Amount of released calcium ions (µg) | | 25 | | 53 | | 102 | | 200 | | 414 | |
| Flexural strength | Immediately after production (MPa) | 78 | | 77 | | 76 | | 75 | | 73 | |
|  | After 10-day storage at 70° C. (MPa) | 75 | | 73 | | 75 | | 73 | | 71 | |
| Bond strength to zirconia | Immediately after production (MPa) | 27 | | 28 | | 26 | | 25 | | 23 | |
|  | After 4000 cycles of thermal cycling (MPa) | 24 | | 25 | | 25 | | 26 | | 20 | |

TABLE 3-2

|  |  |  | Comp. Example 3-1 | | Comp. Example 3-2 | | Comp Example 3-3 | |
|---|---|---|---|---|---|---|---|---|
|  |  |  | Paste A | Paste B | Paste A | Paste B | Paste A | Paste B |
| Raw materials | Polymerizable monomer (a) | D-2.6E (parts by weight) | 55 | 45 | 55 | 45 | 55 | 45 |
|  |  | NPGDMA (parts by weight) | 25 | 35 | 25 | 35 | 25 | 35 |
|  |  | #801 (parts by weight) | — | 20 | — | 20 | — | 20 |
|  | Polymerization initiator (b) | BPO (parts by weight) | 2.0 | — | 2.0 | — | 2.0 | — |
|  |  | CQ (parts by weight) | 0.25 | — | 0.25 | — | 0.25 | — |
|  | Polymerization accelerator | DEPT (parts by weight) | — | 0.3 | — | 0.3 | — | 0.3 |
|  |  | TPSS (parts by weight) | — | 0.5 | — | 0.5 | — | 0.5 |
|  |  | DABE | — | 0.3 | — | 0.3 | — | 0.3 |
|  | Filler (c) | Filler (c-4) (parts by weight) | 200 | — | 200 | — | 200 | — |
|  |  | Filler (c-5) (parts by weight) | 10 | 10 | 10 | 10 | 10 | 10 |
|  |  | Filler (c-6) (parts by weight) | — | 200 | — | 200 | — | 200 |
|  | Acidic group containing polymerizable monomer (d) | MDP (parts by weight) | 20 | — | 20 | — | 20 | — |
|  | Another component | BHT (parts by weight) | 0.05 | 0.05 | 0.05 | 0.05 | 0.05 | 0.05 |
|  | POs-Ca (parts by weight) | | — | — | — | — | — | — |
|  | Calcium hydroxide (parts by weight) | | — | — | — | 10 | — | — |
|  | Calcium chloride (parts by weight) | | — | — | — | — | — | 10 |
| Weight ratio of Paste A/Paste B | | | 1.0 | | 1.0 | | 1.0 | |
| Amount of released calcium ions (µg) | | | 0 | | 40 | | 706 | |
| Flexural strength | Immediately after production (MPa) | | 76 | | 73 | | 71 | |
|  | After 10-day storage at 70° C. (MPa) | | 74 | | 42 | | 11 | |
| Bond strength to zirconia | Immediately after production (MPa) | | 27 | | 23 | | 21 | |
|  | After 4000 cycles of thermal cycling (MPa) | | 25 | | 8 | | 0 | |

Examples 4-1 to 4-4

Glass ionomer cement compositions shown in Table 4, which were prepared by use of the raw materials listed below, were evaluated for their calcium ion release ability, compressive strength, and tensile bond strength to zirconia by employing the testing methods described later.

<Polyalkenoic Acid (e)>

In the case of adding a polyalkenoic acid to a liquid material, a commercially-available polyalkenoic acid (manufactured by NISSEI KAGAKU KOGYO) was used as such. In the case of adding a polyalkenoic acid to a powder material, a polyalkenoic acid powder was obtained by processing a commercially-available polyalkenoic acid (manufactured by NISSEI KAGAKU KOGYO) once with Nano Jetmizer (NJ-100, manufactured by Aishin Nano Technologies CO., LTD.) under conditions where the material feed pressure was 0.7 MPa, the pulverizing pressure was 0.7 MPa, and the processing rate was 8 kg/hr. The average particle diameter of the obtained polyalkenoic acid powder was 3 µm.

<Ion-Leachable Glass (f)>

In a 400 ml milling pot made of alumina ("Type A-3HD Pot Mill" manufactured by Nikkato K.K.) were put 100 g of commercially-available fluoroaluminosilicate glass (G018-117, manufactured by SHOTT AG, Average particle diameter=40.0 µm) and 200 g of zirconia balls with a diameter of 20 mm. The fluoroaluminosilicate glass was pulverized at a rotation speed of 150 rpm for 15 hours to obtain fluoroaluminosilicate glass particles having an average particle diameter of 4 µm.

<Sugar Compound Having —XM Group>

POs-Ca 50: Phosphoryl oligosaccharides of calcium (POs-Ca (registered trademark) 50, manufactured by GLICO NUTRITION CO., LTD.)

[Method for Measuring Calcium Ion Release Ability of Glass Ionomer Cement Composition]

Each glass ionomer cement composition was loaded into a stainless steel mold (with an inner diameter of 15 mm and a thickness of 1 mm). The composition was pressed between glass slides placed on its upper and lower surfaces, then allowed to stand in a thermostat set at 37° C. for 1 hour, and thereby cured. The cured product was removed from the mold, and immersed in 5 ml of ion-exchange water (37° C.). After 28-day immersion, 5 ml of KCl (15 g/L) was added, and calcium ions leached into the ion-exchange water were quantified using a calcium ion electrode (manufactured by HORIBA, Ltd.).

[Method for Measuring Compressive Strength of Glass Ionomer Cement Composition]

Each glass ionomer cement composition was loaded into a stainless steel mold (with an inner diameter of 4 mm and a height of 6 mm). The composition was pressed between glass slides placed on its upper and lower surfaces, then allowed to stand in a thermostat set at 37° C. and 100% RH for 1 hour, and thereby cured. Ten such cured products were prepared, and were stored in 37° C. distilled water for 24 hours after removal from the mold. Five of the cured products were subjected to measurement first. For the measurement, a universal testing machine (Autograph, manufactured by Shimadzu Corporation) was used. The crosshead speed was set to 0.75 mm/min. An average of the measured values was determined as the initial value of the compressive strength of the sample. The other five cured products were stored in 70° C. distilled water for additional 10 days, and then subjected to measurement, so that an index of the durability of the compressive strength was determined.

[Method for Measuring Tensile Bond Strength of Glass Ionomer Cement Composition to Zirconia]

The measurement was performed in the same manner as for the resin cement compositions of Examples 3, except for using the glass ionomer cement compositions instead of the resin cement compositions.

Comparative Examples 4-1 to 4-3

Glass ionomer cement compositions shown in Table 4 were evaluated for their calcium ion release ability, compressive strength, and tensile bond strength to zirconia in the same manner as in Examples 4-1 to 4-4.

Examples 5-1 to 5-4

Resin-modified glass ionomer cement compositions shown in Table 5, which were prepared by use of the raw materials listed below, were evaluated for their calcium ion release ability, flexural strength, bond strength to dentin, and bond strength to zirconia by employing the testing methods described later.

<Polymerizable Monomer (a)>
Bis-GMA: 2,2-bis[4-(3-methacryloyloxy-2-hydroxypropoxy)phenyl]propane
801: 1,2-bis(3-methacryloyloxy-2-hydroxypropyloxy)ethane
HEMA: 2-hydroxyethyl methacrylate <Polymerization Initiator (b)>
KPS: Potassium peroxodisulfate (Average particle diameter=2.5 µm)
DEPT: N,N-bis(2-hydroxyethyl)-p-toluidine <Polymerization Accelerator>
TPSS: Sodium 2,4,6-triisopropylbenzenesulfinate <Acidic Group-Containing Polymerizable Monomer (d)>
MDP: 10-methacryloyloxydecyl dihydrogen phosphate <Polyalkenoic Acid (e)>
The polyalkenoic acid used was obtained by processing a commercially-available polyalkenoic acid (manufactured by NISSEI KAGAKU KOGYO) once with Nano Jetmizer (NJ-100, manufactured by Aishin Nano Technologies CO., LTD) under conditions where the material feed pressure was 0.7 MPa, the pulverizing pressure was 0.7 MPa, and the processing rate was 8 kg/hr. The average particle diameter of the obtained polyalkenoic acid powder was 3 µm.

<Ion-Leachable Glass (f)>
In a 400 ml milling pot made of alumina ("Type A-3HD Pot Mill" manufactured by Nikkato K.K.) were put 100 g of commercially-available fluoroaluminosilicate glass (G018-117, manufactured by SHOTT AG, Average particle diameter=40.0 µm) and 200 g of zirconia balls with a diameter of 20 mm. The fluoroaluminosilicate glass was pulverized at a rotation speed of 150 rpm for 15 hours to obtain fluoroaluminosilicate glass particles having an average particle diameter of 4 µm.

<Another Component>
Water: Commercially-available purified water (manufactured by Takasugi Pharmaceutical Co., Ltd.) complying with the Japanese Pharmacopoeia was used as such.

TABLE 4

|  |  |  | Example 4-1 | Example 4-2 | Example 4-3 | Example 4-4 | Comp. Example 4-1 | Comp. Example 4-2 | Comp. Example 4-3 |
|---|---|---|---|---|---|---|---|---|---|
| Liquid material | Polyalkenoic acid (e) | 65 wt % aqueous solution of polyalkenoic acid (parts by weight) | 90 | 90 | 90 | 90 | 90 | 90 | 90 |
|  | Another component | Tartaric acid (parts by weight) | 10 | 10 | 10 | 10 | 10 | 10 | 10 |
| Powder material | Ion-leachable glass (f) | Fluoroaluminosilicate glass particles (parts by weight) | 90 | 90 | 90 | 90 | 90 | 90 | 90 |
|  | Polyalkenoic acid (e) | Polyalkenoic acid powder (parts by weight) | 10 | 10 | 10 | 10 | 10 | 10 | 10 |
|  | POs-Ca (parts by weight) |  | 0.5 | 1 | 2 | 5 | — | — | — |
|  | Calcium hydroxide (parts by weight) |  | — | — | — | — | — | 1 | — |
|  | Calcium chloride (parts by weight) |  | — | — | — | — | — | — | 1 |
|  | Powder/Liquid weight ratio |  | 1.8 | 1.8 | 1.8 | 1.8 | 1.8 | 1.8 | 1.8 |
|  | Amount of released calcium ions (µg) |  | 34 | 65 | 152 | 205 | 0 | 11 | 72 |
| Compressive strength | Immediately after production (MPa) |  | 131 | 133 | 132 | 128 | 131 | 130 | 128 |
|  | After 10-day storage at 70° C. (MPa) |  | 129 | 129 | 130 | 126 | 130 | 22 | 5 |
| Bond strength to zirconia | Immediately after production (MPa) |  | 9 | 9 | 10 | 7 | 8 | 7 | 6 |
|  | After 4000 cycles of thermal cycling (MPa) |  | 8 | 7 | 7 | 5 | 6 | 0 | 0 |

<Another Component: Polymerization Inhibitor>
BHT: 2,6-di-t-butyl-4-methylphenol
<Sugar Compound Having —XM Group>
POs-Ca: Phosphoryl oligosaccharides of calcium (POs-Ca (registered trademark) 50, manufactured by GLICO NUTRITION CO., LTD.)

[Method for Measuring Calcium Ion Release Ability of Resin-Modified Glass Ionomer Cement Composition]

Each resin-modified glass ionomer cement composition was loaded into a stainless steel mold (with an inner diameter of 15 mm and a thickness of 1 mm). The composition was pressed between glass slides placed on its upper and lower surfaces, then allowed to stand in a thermostat set at 37° C. for 1 hour, and thereby cured. The cured product was removed from the mold, and immersed in 5 ml of ion-exchange water (37° C.). After 28-day immersion, 5 ml of KCl (15 g/L) was added, and calcium ions leached into the ion-exchange water were quantified using a calcium ion electrode (manufactured by HORIBA, Ltd.).

[Method for Measuring Flexural Strength of Resin-Modified Glass Ionomer Cement Composition]

Each resin-modified glass ionomer cement composition was loaded into a stainless steel mold (with inner dimensions of 2 mm×2 mm×20 mm). The composition was pressed between glass slides placed on its upper and lower surfaces, then allowed to stand in a thermostat set at 37° C. for 1 hour, and thereby cured. Ten such cured products were prepared, and were stored in 37° C. distilled water for 24 hours after removal from the mold. Five of the cured products were subjected to measurement first. For the measurement, a universal testing machine (Autograph, manufactured by Shimadzu Corporation) was used. The span was set to 20 mm, and the crosshead speed was set to 1 mm/min. An average of the measured values was determined as the initial value of the flexural strength of the sample. The other five cured products were stored in 70° C. distilled water for additional 10 days, and then subjected to measurement, so that an index of the durability of the flexural strength was determined.

[Method for Measuring Tensile Bond Strength of Resin-Modified Glass Ionomer Cement Composition to Dentin]

The labial surface of a bovine mandibular incisor was ground with #80 silicon carbide paper (manufactured by NIHON KENSHI CO., LTD.) under running water so as to expose a flat surface of dentin. Thus, a sample was obtained. The sample obtained was further ground with #1000 silicon carbide paper (manufactured by NIHON KENSHI CO., LTD.) under running water. After the completion of grinding, the sample was dried by removing water from its surface by air-blowing. To the dried smooth surface was attached an about 150-μm-thick adhesive tape having a circular hole of 3-mm diameter, so that an adhesive area was delimited.

The resin-modified glass ionomer cement composition was mounded on one end face (circular end face) of a cylindrical stainless steel rod (with a diameter of 7 mm and a length of 2.5 cm). The end face with the paste mounded thereon was placed on the smooth surface (adherend) within the circular hole in such a manner that the center of the circular hole and the center of the cylindrical stainless steel rod substantially coincided with each other. The cylindrical stainless steel rod was perpendicularly pressed against and bonded to the smooth surface, and thus a testing sample was prepared. There were prepared 14 such testing samples. An excess portion of the paste that spread out of the perimeter of the cylindrical stainless steel rod during the pressing was removed, then the testing samples were allowed to stand at room temperature for 30 minutes and immersed in distilled water. The testing samples immersed in distilled water were allowed to stand in a thermostat maintained at 37° C. for 24 hours, after which seven of the samples were taken out and examined for their tensile bond strength. The tensile bond strength was measured using a universal testing machine (Autograph, manufactured by Shimadzu Corporation) and setting the crosshead speed to 2 mm/min. An average of the measured values was determined as the initial value of the tensile bond strength to dentin.

The other seven samples were subjected to thermal cycling in which they were immersed alternately in a 4° C. water bath and a 60° C. water bath for 1 minute each. After 4000 cycles of the thermal cycling, the tensile bond strength of each sample was measured, and an average of the measured values was determined as an index of the durability of the tensile bond strength to dentin.

[Method for Measuring Tensile Bond Strength of Resin-Modified Glass Ionomer Cement Composition to Zirconia]

The measurement was performed in the same manner as for the resin cement compositions of Examples 3, except for using the resin-modified glass ionomer cement compositions instead of the resin cement compositions.

Comparative Examples 5-1 to 5-3

Resin-modified glass ionomer cement compositions shown in Table 5 were evaluated for their calcium ion release ability, flexural strength, bond strength to dentin, and bond strength to zirconia in the same manner as in Examples 5-1 to 5-4.

TABLE 5

| | | | | Example 5-1 | Example 5-2 | Example 5-3 | Example 5-4 | Comp. Example 5-1 | Comp. Example 5-2 | Comp. Example 5-3 |
|---|---|---|---|---|---|---|---|---|---|---|
| Raw materials | Liquid material | Polymerizable monomer (a) | Bis-GMA (parts by weight) | 52 | 52 | 52 | 52 | 52 | 52 | 52 |
| | | | #801 (parts by weight) | 5 | 5 | 5 | 5 | 5 | 5 | 5 |
| | | | HEMA (parts by weight) | 35 | 35 | 35 | 35 | 35 | 35 | 35 |
| | | Polymerization accelerator | DEPT (parts by weight) | 0.3 | 0.3 | 0.3 | 0.3 | 0.3 | 0.3 | 0.3 |
| | | Acidic group containing polymerizable monomer (d) | MDP (parts by weight) | 3 | 3 | 3 | 3 | 3 | 3 | 3 |
| | | Other components | Water (parts by weight) | 5 | 5 | 5 | 5 | 5 | 5 | 5 |
| | | | BHT (parts by weight) | 0.05 | 0.05 | 0.05 | 0.05 | 0.05 | 0.05 | 0.05 |
| | Powder material | Ion-leachable glass (f) | Fluoroaluminosilicate glass particles (parts by weight) | 90 | 90 | 90 | 90 | 90 | 90 | 90 |

TABLE 5-continued

| | | Example 5-1 | Example 5-2 | Example 5-3 | Example 5-4 | Comp. Example 5-1 | Comp. Example 5-2 | Comp. Example 5-3 |
|---|---|---|---|---|---|---|---|---|
| Polyalkenoic acid (e) | Polyalkenoic acid powder (parts by weight) | 10 | 10 | 10 | 10 | 10 | 10 | 10 |
| Polymerization initiator (b) | KPS (parts by weight) | 1 | 1 | 1 | 1 | 1 | 1 | 1 |
| Polymerization accelerator | TPSS (parts by weight) | 1 | 1 | 1 | 1 | 1 | 1 | 1 |
| | POs-Ca (parts by weight) | 0.5 | 1 | 5 | 10 | — | — | — |
| | Calcium hydroxide (parts by weight) | — | — | — | — | — | 5 | — |
| | Calcium chloride (parts by weight) | — | — | — | — | — | — | 5 |
| | Powder/Liquid weight ratio | 1.6 | 1.6 | 1.6 | 1.6 | 1.6 | 1.6 | 1.6 |
| | Amount of released calcium ions (μg) | 39 | 63 | 280 | 398 | 0 | 52 | 249 |
| Flexural strength | Immediately after production (MPa) | 46 | 47 | 45 | 41 | 46 | 44 | 43 |
| | After 10-day storage at 70° C. (MPa) | 43 | 44 | 43 | 38 | 44 | 22 | 5 |
| Bond strength to dentin | Immediately after production (MPa) | 7 | 6 | 6 | 6 | 7 | 5 | 5 |
| | After 4000 cycles of thermal cycling (MPa) | 5 | 6 | 5 | 4 | 6 | 3 | 0 |
| Bond strength to zirconia | Immediately after production (MPa) | 27 | 28 | 26 | 22 | 27 | 24 | 23 |
| | After 4000 cycles of thermal cycling (MPa) | 25 | 26 | 25 | 19 | 26 | 6 | 2 |

As indicated in the above tables, the cured products of the dental curable compositions of the present invention which were prepared in Examples showed high calcium ion release ability; in addition, their physical properties such as flexural strength, compressive strength, and bond strength were comparable to those exhibited when no calcium compound was added, and the durability of the physical properties was also excellent. Although the details of the causal mechanism have yet to be defined, it can be inferred that, along with leaching of metal cations, acid anion group moieties, which act as counter ions of the metal cations, are adsorbed on polar group moieties of a matrix component of the cured product of the curable composition or on metal element moieties of the surface of the filler in the cured product so that the sugar chain structure is formed to serve as a crosslinking agent within the cured product, thereby compensating for the decrease in strength associated with defect formation due to the metal cation release.

By contrast, as indicated in the above tables, the samples of Comparative Examples for which calcium hydroxide was added had lower calcium release ability than those of Examples, and also were obviously inferior in the durability of the physical properties. The samples of Comparative Examples for which calcium chloride was added had very high calcium release ability by virtue of the high water solubility of calcium chloride; however, they showed marked deterioration in physical properties after stored in water.

INDUSTRIAL APPLICABILITY

The dental curable composition of the present invention can be used as any of various dental materials such as a dental composite resin, a dental adhesive, a dental resin cement, a dental glass ionomer cement, a dental resin-modified glass ionomer cement, and a dental quick cure resin which are used in a dental restorative filling material, a dental adhesive material, a dental luting material, a dental temporary sealing material, a dental provisional crown material, and a dental pit and fissure sealant.

The invention claimed is:

1. A dental curable composition comprising: a sugar compound having an —XM group and a curable component, wherein the curable component comprises a polymerizable monomer (a) having no acidic group and a polymerization initiator (b), and wherein,
    —X in the —XM group of the sugar compound is at least one acid anion group selected from the group consisting of; phosphorus atom-containing acid anion groups represented by —P(=O)(—O$^-$)$_2$, —P(=O)(—OR)(—O$^-$), —O—P(=O)(—O$^-$)$_2$, and —O—P(=O)(—OR)(—O$^-$), where R represents an alkyl group or an aromatic group optionally substituted with an alkyl group having 1 to 3 carbon atoms or with a halogen atom; sulfur atom-containing acid anion groups represented by —SO$_2$$^-$, —SO$_3$$^-$ and —O—SO$_3$$^-$; and boron atom-containing acid anion groups represented by —B(O$^-$)$_2$, —O—B(O$^-$)$_2$, —B(—OR)(O$^-$), and —O—B(—OR)(O$^-$), where R represents an alkyl group or an aromatic group optionally substituted with an alkyl group having 1 to 3 carbon atoms or with a halogen atom, and
    M in the —XM group of the sugar compound is a calcium ion, a strontium ion, or an aluminum ion.,
    the content of the sugar compound having the —KM group is 0.01 to 30 weight% relative to the total amount of the composition,
    the polymerizable monomer (a) is at least one selected from the group consisting of a (meth)acrylic acid ester and a (meth)acrylamide derivative,
    wherein the (meth)acrylamide derivative is at least one selected from the group consisting of N-methylol (meth)acrylamide, N-hydroxyethyl (meth)acrylamide, and N-(dihydroxyethyl) (meth)acrylamide.

2. The dental curable composition according to claim 1, wherein the sugar compound having the —XM group is a calcium sugar phosphate.

3. The dental curable composition according to claim 1, containing 0.01 to 10 weight% of the sugar compound having the —XM group.

4. The dental curable composition according to claim 1, wherein the curable component further comprises an acidic group-containing polymerizable monomer(d).

5. The dental curable composition according to claim 1, further comprising a filler (c).

6. The dental curable composition according to claim 1, wherein the curable component comprises a polyalkenoic acid (e), ion-leachable glass (f), and water (g).

7. The dental curable composition according to claim 1, wherein the curable component further comprises an acidic group-containing polymerizable monomer (d).

8. The dental curable composition according to claim 1, being a dental restorative filling material.

9. The dental curable composition according to claim 1, being a dental adhesive material.

10. The dental curable composition according to claim 1, being a dental luting material.

11. The dental curable composition according to claim 1, being a dental temporary sealing material.

12. The dental curable composition according to claim 1, being a dental pit and fissure sealant.

13. The dental curable composition according to claim 1, wherein the content of the sugar compound having the —XM group is 0.05 to 20 weight% relative to the total amount of the composition.

14. The dental curable composition according to claim 1, wherein the (meth)acrylic acid ester comprises an aromatic-based difunctional polymerizable monomer.

* * * * *